United States Patent
Liu et al.

(10) Patent No.: US 7,709,461 B2
(45) Date of Patent: May 4, 2010

(54) METHODS AND PRODUCTS RELATED TO PULMONARY DELIVERY OF POLYSACCHARIDES

(75) Inventors: Dongfang Liu, Framingham, MA (US); Yiwei Qi, Framingham, MA (US); Ganesh Venkataraman, Woburn, MA (US); Mallikarjun Sundaram, Brighton, MA (US); Ram Sasisekharan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/982,548

(22) Filed: Oct. 18, 2001

(65) Prior Publication Data

US 2002/0128225 A1    Sep. 12, 2002

Related U.S. Application Data

(60) Provisional application No. 60/241,559, filed on Oct. 18, 2000.

(51) Int. Cl.
*A61K 31/715* (2006.01)
*A01N 43/04* (2006.01)

(52) U.S. Cl. .......................................... 514/54; 514/56
(58) Field of Classification Search .............. 514/54–61
See application file for complete search history.

(56) References Cited

U.S. PATENT DOCUMENTS

| | | |
|---|---|---|
| 4,281,108 A | 7/1981 | Fussi |
| 4,341,869 A | 7/1982 | Langer, Jr. et al. |
| 4,373,023 A | 2/1983 | Langer et al. |
| 4,396,762 A | 8/1983 | Langer et al. |
| 4,443,545 A | 4/1984 | Langer, Jr. et al. |
| 4,551,296 A | 11/1985 | Kavesh et al. |
| 4,679,555 A * | 7/1987 | Sackner et al. |
| 4,745,105 A | 5/1988 | Griffin et al. |
| 4,757,056 A | 7/1988 | Van Gorp et al. |
| 4,830,013 A | 5/1989 | Maxwell |
| 4,928,694 A | 5/1990 | Maxwell |
| 4,942,156 A | 7/1990 | Foley et al. |
| 4,990,502 A | 2/1991 | Lormeau et al. |
| 5,010,063 A | 4/1991 | Piani et al. |
| 5,039,529 A | 8/1991 | Bergendal et al. |
| 5,106,734 A | 4/1992 | Nielsen |
| 5,152,784 A | 10/1992 | Tsilibary |
| 5,164,378 A | 11/1992 | Conti et al. |
| 5,169,772 A | 12/1992 | Zimmerman et al. |
| 5,204,323 A | 4/1993 | Findlay et al. |
| 5,252,339 A | 10/1993 | Cristofori et al. |
| 5,262,325 A | 11/1993 | Zimmermann et al. |
| 5,290,695 A | 3/1994 | Morikawa et al. |
| 5,338,677 A | 8/1994 | Zimmermann et al. |
| 5,389,539 A | 2/1995 | Sasisekharan et al. |
| 5,453,171 A | 9/1995 | Ma et al. |
| 5,474,987 A | 12/1995 | Cohen et al. |
| 5,527,532 A * | 6/1996 | Edelman et al. .............. 424/422 |
| 5,567,417 A | 10/1996 | Sasisekharan et al. |
| 5,569,366 A | 10/1996 | Chen et al. |
| 5,569,600 A | 10/1996 | Sasisekharan et al. |
| 5,576,304 A | 11/1996 | Kakkar et al. |
| 5,597,811 A * | 1/1997 | Gruber ........................ 514/55 |
| 5,599,801 A | 2/1997 | Branellec et al. |
| 5,607,859 A | 3/1997 | Biemann et al. |
| 5,618,917 A | 4/1997 | Toback et al. |
| 5,619,421 A | 4/1997 | Venkataraman et al. |
| 5,681,733 A | 10/1997 | Su et al. |
| 5,687,090 A | 11/1997 | Chen et al. |
| 5,714,376 A | 2/1998 | Sasisekharan et al. |
| 5,744,515 A | 4/1998 | Clapper |
| 5,752,019 A | 5/1998 | Rigoutsos et al. |
| 5,753,445 A | 5/1998 | Fillit et al. |
| 5,759,767 A | 6/1998 | Lakowicz et al. |
| 5,763,427 A | 6/1998 | Weitz et al. |
| 5,767,269 A | 6/1998 | Hirsh et al. |
| 5,776,434 A | 7/1998 | Purewal et al. |
| 5,795,875 A | 8/1998 | Holme et al. |
| 5,808,021 A | 9/1998 | Holme et al. |
| 5,824,299 A | 10/1998 | Luster et al. |
| 5,830,726 A | 11/1998 | Sasisekharan et al. |
| 5,855,913 A | 1/1999 | Hanes et al. |
| 5,874,064 A | 2/1999 | Edwards et al. |
| 5,879,713 A | 3/1999 | Roth et al. |
| 5,919,693 A | 7/1999 | Su et al. |
| 5,922,358 A | 7/1999 | Doutremepuich et al. |
| 5,952,653 A | 9/1999 | Covey et al. |
| 5,968,822 A | 10/1999 | Pecker et al. |
| 5,985,309 A | 11/1999 | Edwards et al. |
| 5,990,097 A | 11/1999 | Kennedy |
| 5,993,783 A | 11/1999 | Eljamal et al. |
| 5,993,846 A | 11/1999 | Friedman et al. |
| 5,997,863 A | 12/1999 | Zimmermann et al. |
| 6,013,628 A | 1/2000 | Skubitz et al. |
| 6,019,968 A | 2/2000 | Platz et al. |
| 6,051,256 A | 4/2000 | Platz et al. |
| 6,116,237 A | 9/2000 | Schultz et al. |
| 6,123,936 A | 9/2000 | Platz et al. |

(Continued)

FOREIGN PATENT DOCUMENTS

EP          0 140 781           5/1985

(Continued)

OTHER PUBLICATIONS

Kreitz, M.R. et al. (1997) "Controlled delivery of therapeutics from microporous membranes. II. In vitro degradation and release of heparin-loaded poly(D,L-lactide-co-glycolide)", *Biomaterials* 18:1645.

(Continued)

*Primary Examiner*—Traviss C McIntosh, III
(74) *Attorney, Agent, or Firm*—Wolf, Greenfield & Sacks, P.C.

(57) ABSTRACT

The invention relates to methods for delivering polysaccharides by a pulmonary route to achieve local and systemic therapeutic effects. The polysaccharides may be formulated or unformulated and in some instances have an extremely fast absorption rate.

24 Claims, 7 Drawing Sheets

U.S. PATENT DOCUMENTS

| | | | |
|---|---|---|---|
| 6,136,295 | A | 10/2000 | Edwards et al. |
| 6,165,463 | A | 12/2000 | Platz et al. |
| RE37,053 | E | 2/2001 | Hanes et al. |
| 6,190,875 | B1 | 2/2001 | Ben-Artzi et al. |
| 6,217,863 | B1 | 4/2001 | Godavarti et al. |
| 6,231,851 | B1 | 5/2001 | Platz et al. |
| 6,268,146 | B1 | 7/2001 | Shultz et al. |
| 6,291,439 | B1 | 9/2001 | Klock |
| 6,309,853 | B1 | 10/2001 | Friedman et al. |
| 6,333,051 | B1 | 12/2001 | Kabanov et al. |
| 6,569,458 | B1* | 5/2003 | Gombotz et al. ............. 424/489 |
| 6,597,996 | B1 | 7/2003 | Venkataraman et al. |
| 6,869,789 | B2 | 3/2005 | Liu et al. |
| 6,962,699 | B2 | 11/2005 | Pojasek et al. |
| 7,056,504 | B1 | 6/2006 | Sasisekharan et al. |
| 7,083,937 | B2 | 8/2006 | Sasisekharan et al. |
| 7,105,334 | B2 | 9/2006 | Pojasek et al. |
| 7,110,889 | B2 | 9/2006 | Venkataraman et al. |
| 7,117,100 | B2 | 10/2006 | Venkataraman et al. |
| 7,129,335 | B2 | 10/2006 | Pojasek et al. |
| 7,139,666 | B2 | 11/2006 | Venkataraman |
| 7,247,445 | B2 | 7/2007 | Sasisekharan et al. |
| 7,270,815 | B2 | 9/2007 | Sasisekharan et al. |
| 7,390,633 | B2 | 6/2008 | Liu et al. |
| 7,396,824 | B2 | 7/2008 | Sasisekharan et al. |
| 7,399,604 | B2 | 7/2008 | Sasisekharan et al. |
| 7,412,332 | B1 | 8/2008 | Venkataraman et al. |
| 7,429,474 | B2 | 9/2008 | Sasisekharan et al. |
| 7,455,986 | B2 | 11/2008 | Liu et al. |
| 7,504,247 | B2 | 3/2009 | Sasisekharan et al. |
| 7,507,570 | B2 | 3/2009 | Prabhakar et al. |
| 7,508,206 | B2 | 3/2009 | Sasisekharan et al. |
| 7,553,950 | B2 | 6/2009 | Prabhakar et al. |
| 7,560,106 | B2 | 7/2009 | Sasisekharan et al. |
| 7,585,642 | B2 | 9/2009 | Sasisekharan et al. |
| 2002/0122793 | A1 | 9/2002 | Liu et al. |
| 2002/0128225 | A1 | 9/2002 | Liu et al. |
| 2002/0169143 | A1 | 11/2002 | Sasisekharan et al. |
| 2003/0008820 | A1 | 1/2003 | Kwan et al. |
| 2003/0068279 | A1 | 4/2003 | Platz et al. |
| 2003/0086877 | A1 | 5/2003 | Platz et al. |
| 2003/0099628 | A1 | 5/2003 | Liu et al. |
| 2003/0191587 | A1 | 10/2003 | Venkataraman et al. |
| 2003/0198601 | A1 | 10/2003 | Platz et al. |
| 2004/0091471 | A1 | 5/2004 | Myette et al. |
| 2004/0091472 | A1 | 5/2004 | Pojasek et al. |
| 2004/0092037 | A1 | 5/2004 | Sasisekharan et al. |
| 2004/0197933 | A1 | 10/2004 | Venkataraman et al. |
| 2004/0204869 | A1 | 10/2004 | Venkataraman et al. |
| 2005/0037376 | A1 | 2/2005 | Sasisekharan et al. |
| 2005/0214276 | A9 | 9/2005 | Myette et al. |
| 2005/0227320 | A1 | 10/2005 | Pojasek et al. |
| 2005/0233402 | A1 | 10/2005 | Liu et al. |
| 2005/0233419 | A1 | 10/2005 | Pojasek et al. |
| 2006/0024664 | A1 | 2/2006 | Sasisekharan et al. |
| 2006/0057638 | A1 | 3/2006 | Bosques et al. |
| 2006/0067927 | A1 | 3/2006 | Chandrasekaran et al. |
| 2006/0067928 | A1 | 3/2006 | Liu et al. |
| 2006/0078959 | A1 | 4/2006 | Prabhakar et al. |
| 2006/0083711 | A1 | 4/2006 | Berry et al. |
| 2006/0105430 | A1 | 5/2006 | Sasisekharan et al. |
| 2006/0127950 | A1 | 6/2006 | Bosques et al. |
| 2006/0154894 | A1 | 7/2006 | Berry et al. |
| 2006/0177885 | A1 | 8/2006 | Myette et al. |
| 2006/0177910 | A1 | 8/2006 | Myette et al. |
| 2006/0177911 | A1 | 8/2006 | Myette et al. |
| 2006/0182734 | A1 | 8/2006 | Liu et al. |
| 2006/0183713 | A1 | 8/2006 | Liu et al. |
| 2006/0183891 | A1 | 8/2006 | Myette et al. |
| 2006/0292130 | A1 | 12/2006 | Sasisekharan et al. |
| 2006/0292655 | A1 | 12/2006 | Sasisekharan et al. |
| 2006/0292673 | A1 | 12/2006 | Sasisekharan et al. |
| 2007/0004012 | A1 | 1/2007 | Sasisekharan et al. |
| 2007/0020243 | A1 | 1/2007 | Sengupta et al. |
| 2007/0065424 | A1 | 3/2007 | Pojasek et al. |
| 2007/0065921 | A1 | 3/2007 | Sasisekharan et al. |
| 2007/0066769 | A1 | 3/2007 | Venkataraman et al. |
| 2007/0148157 | A1 | 6/2007 | Prabhakar et al. |
| 2007/0148158 | A1 | 6/2007 | Sasisekharan et al. |
| 2007/0148740 | A1 | 6/2007 | Prabhakar et al. |
| 2007/0161073 | A1 | 7/2007 | Sasisekharan et al. |
| 2007/0202563 | A1 | 8/2007 | Prabhakar et al. |
| 2007/0224670 | A1 | 9/2007 | Prabhakar et al. |
| 2008/0071148 | A1 | 3/2008 | Bosques et al. |
| 2008/0278164 | A1 | 11/2008 | Sasisekharan et al. |
| 2008/0301178 | A1 | 12/2008 | Venkataraman et al. |
| 2009/0045811 | A1 | 2/2009 | Sasisekharan et al. |
| 2009/0081635 | A1 | 3/2009 | Liu et al. |
| 2009/0105463 | A1 | 4/2009 | Berry et al. |
| 2009/0119027 | A1 | 5/2009 | Venkataraman et al. |
| 2009/0156477 | A1 | 6/2009 | Berry et al. |

FOREIGN PATENT DOCUMENTS

| | | |
|---|---|---|
| EP | 0208623 A2 | 1/1987 |
| EP | 0 114 589 B1 | 9/1987 |
| EP | 0 244 236 A2 | 11/1987 |
| EP | 0 394 971 A1 | 10/1990 |
| EP | 0 433 225 A1 | 6/1991 |
| EP | 0 342 215 B1 | 8/1993 |
| EP | 0 557 887 A2 | 9/1993 |
| JP | 62-018401 A | 1/1987 |
| JP | 08-511764 A2 | 2/1994 |
| JP | 2000-511189 A1 | 11/1997 |
| JP | 2001-526634 | 12/2001 |
| WO | WO 92/01003 A1 | 1/1992 |
| WO | WO 93/05167 A1 | 3/1993 |
| WO | WO 93/08289 A1 | 4/1993 |
| WO | WO 93/10450 A1 | 5/1993 |
| WO | WO 93/15406 A1 | 8/1993 |
| WO | WO 93/19096 A1 | 9/1993 |
| WO | 93/19734 | 10/1993 |
| WO | WO 93/19734 | 10/1993 |
| WO | WO 94/12618 A1 | 6/1994 |
| WO | WO 94/21689 A1 | 9/1994 |
| WO | WO 95/13830 A1 | 5/1995 |
| WO | 95/21198 A2 | 8/1995 |
| WO | WO 95/34635 A1 | 12/1995 |
| WO | WO 96/01648 A1 | 1/1996 |
| WO | 96/32149 | 10/1996 |
| WO | WO 96/32149 * | 10/1996 |
| WO | 97/06783 | 2/1997 |
| WO | WO 97/06783 | 2/1997 |
| WO | WO 97/11684 A1 | 4/1997 |
| WO | WO 97/16556 A1 | 5/1997 |
| WO | 97/35562 | 10/1997 |
| WO | WO 97/35562 * | 10/1997 |
| WO | WO 98/04902 A1 | 2/1998 |
| WO | 98/31346 | 7/1998 |
| WO | WO 98/31346 * | 7/1998 |
| WO | WO 00/12726 A2 | 3/2000 |
| WO | WO 00/65521 A2 | 11/2000 |
| WO | 01/66772 A2 | 9/2001 |
| WO | 02/23190 A2 | 3/2002 |
| WO | 02/32406 A2 | 4/2002 |
| WO | 02/077199 A2 | 10/2002 |
| WO | WO 03/068187 A1 | 8/2003 |
| WO | WO 03/068188 A1 | 8/2003 |
| WO | 03/102160 A3 | 12/2003 |
| WO | 2004/055491 A2 | 7/2004 |
| WO | 2004/062592 A2 | 7/2004 |
| WO | 2004/069152 A2 | 8/2004 |
| WO | 2005/087920 A2 | 9/2005 |
| WO | 2005/110438 A2 | 11/2005 |

| WO | 2005/111627 A2 | 11/2005 |
| WO | 2006/076627 A2 | 7/2006 |
| WO | 2006/083328 A2 | 8/2006 |
| WO | 2006/088491 A2 | 8/2006 |
| WO | 2006/105313 A2 | 10/2006 |
| WO | 2006/105315 A2 | 10/2006 |
| WO | 2007/044471 A2 | 4/2007 |
| WO | 2007/120478 A2 | 10/2007 |

OTHER PUBLICATIONS

Ameer et al., "A New Approach to Regional Heparinization: Design and Development of a Novel Immobilized Heparinase Device", *Blood Purification Meeting Information: The International Conference on Continuous Renal Replacement Therapies*, 16(2):107-108, 1998. Abstract Only.

Baumann et al., "Three-dimensional Structure of the Alkaline Protease of *Pseudomonas aeruginosa*: A Two-domain Protein with a Calcium Binding Parallel Beta Roll Motif", *The EMBO Journal*, 12(9): 3357-3364, 1993.

Berry et al., "Distinct Heparan Sulfate Glycosaminoglycans are Responsible for Mediating Fibroblast Growth Factor-2 Biological Activity Through Different Fibroblast Growth Factor Receptors", *The FASEB Journal*, Express Article No. 10.1096/fj.00-0661fje: 1-19, 2001.

Biemann, "Four Decades of Structure Determination by Mass Spectrometry: From Alkaloids to Heparin", *J. Am. Soc. Mass. Spectrom.*, 13: 1254-1272, 2002.

Carlson et al., "Behavior of Antithrombin III Isoforms on Immobilized Heparins: Evidence that the Isoforms Bind to Different Numbers of Low-affinity Heparin Sites", *The Journal of Biological Chemistry*, 263(5):2187-2194, 1988.

Claverie et al., "Information Enhancement Methods for Large Scale Sequence Analysis", *Computers Chem.*, 17(2): 191-201, 1993.

Cohen, "The Parallel β Helix of Pectate Lyase C: Something to Sneeze At", *Science*, 260: 1444-1445, 1993.

Crum et al., "A New Class of Steroids Inhibits Angiogenesis in the Presence of Heparin or a Heparin Fragment", *Science*, 230: 1375-1378, 1985.

Dull et al., "Lung Endothelial Heparan Sulfates Mediate Cationic Peptide-induced Barrier Dysfunction: A New Role for the Glycocalyx", *Am. J. Physiol. Lung Cell Mol. Physiol.*, 285: L986-L995, 2003.

Ernst et al., "Expression in *Escherichia coli*, Purification and Characterization of Heparinase I from *Flavobacterium heparinum*", *Biochem. J.*, 315: 589-597, 1996.

Ernst et al., "Enzymatic Degradation of Glycosaminoglycans", *Critical Reviews in Biochemistry and Molecular Biology*, 30(5): 387-444, 1995.

Folkman et al., "Angiogenesis Inhibition and Tumor Regression Caused by Heparin or a Heparin Fragment in the Presence of Cortisone", *Science*, 221:719-725, 1983.

Franklin et al., "*Pseudomonas aeruginosa AlgG* is a Polymer Level Alginate C5-Mannuronan Epimerase", *Journal of Bacteriology*, 176(7): 1821-1830, 1994.

Gacesa, "Alginate-modifying Enzymes: A Proposed Unified Mechanism of Action for the Lyases and Epimerases", *Febs Letters*, 212(2):199-202, 1987.

Gioldassi et al., "Determination of Phosphorylated and Sulfated Linkage-region Oligosaccharides in Chondroitin / Dermatan and Heparan Sulfate Proteoglycans by High Performance Liquid Chromatography", *J. Liq. Chrom. & Rel. Technol.*, 22(13): 1997-2007, 1999.

Godavarti et al., "Heparinase I from *Flavobacterium heparinum*: Role of Positive Charge in Enzymatic Activity", *The Journal of Biological Chemistry*, 273(1): 248-255, 1998.

Guerrini et al., "A Novel Computational Approach to Integrate NMR Spectroscopy and Capillary Electrophoresis for Structure Assignment of Heparin and Heparan Sulfate Oligosaccharides", *Glycobiology*, 12(11): 713-719, 2002.

Hayes, "Prototeins", *American Scientist, the Magazine of Sigma Xi, the Scientific Research Society*, 86(3): 216-221, 1998.

Higuchi, "Recombinant PCR", *PCR Protocols: A Guide to Methods and Applications*, Academic Press, Inc., NY: 1990, Chapter 22, 177-183.

Horner et al., "Heterogeneity of Rat Skin Heparin Chains with High Affinity for Antithrombin", *Biochem. J.*, 244: 693-698, 1987.

Johnson et al., "Endothelial Cells Preparing to Die by Apoptosis Initiate a Program of Transcriptome and Glycome Regulation", *The FASEB Journal*, 18: 188-190, 2004.

Keiser et al., "Direct Isolation and Sequencing of Specific Protein-binding Glycosaminoglycans", *Nature Medicine*, 7(1): 123-128, 2001.

Kishibe et al., "Structural Requirements of Heparan Sulfate for the Binding to the Tumor-derived Adhesion Factor/ Angiomodulin that Induces Cord-like Structures to ECV-304 Human Carcinoma Cells", *The Journal of Biological Chemistry*, 275(20): 15321-15329, 2000.

Leckband et al., "Characterization of the Active Site of Heparinase", *Abstracts of Papers Part 1: Fourth Chemical Congress of North America*, 202(1): a56, 1991.

Lewin, *Genes V*, p. 13, 1994.

Liu, Dongfang, et al., "Dynamic Regulation of Tumor Growth and Metastasis by Heparan Sulfate Glycosaminoglycans", *Seminars in Thrombosis and Hemostasis*, 28(1): 67-78, 2002.

Liu, Dongfang, et al, "Tumor Cell Surface Heparan Sulfate as Cryptic Promoters or Inhibitors of Tumor Growth and Metastasis", *PNAS*, 99(2): 568-573, 2002.

Liu, Jian, et al., "Strategy for the Sequence Analysis of Heparin", *Glycobiology*, 5(8): 765-774, 1995.

Liu, Jian, et al., "Characterization of a Heparan Sulfate Octasaccharide that Binds to Herpes Simplex Virus Type 1 Glycoprotein D", *The Journal of Biological Chemistry*, 277(36): 33456-33467, 2002.

Marciniak, "Differential Role of Fractionated Heparin in Antithrombin-III Proteolysis", *Blood*, 59(3): 576- 581, 1982.

McLean et al., "Enzymic Removal of 2-$O$-Sulphato-$\Delta_{4,5}$-Glycuronic Acid Residues from Heparin Oligosaccharides", *Proc. of the 7$^{th}$ Int'l. Symposium of Glycoconjugates*, p. 68-69, 1983.

Murphy et al., "Basic Fibroblast Growth Factor Binding and Processing by Human Glioma Cells", *Molecular and Cellular Endocrinology*, 114: 193-203, 1995.

Myette et al., "The Heparin / Heparan Sulfate 2-$O$-Sulfatase from *Flavobacterium heparinum*", *The Journal of Biological Chemistry*, 278(14): 12157-12166,2003.

Myette et al., "Molecular Cloning of the Heparin / Heparan Sulfate $\Delta_{4,5}$ Unsaturated Glycuronidase from *Flavobacterium heparinum*, its Recombinant Expression in *Escherichia coli*, and Biochemical Determination of its Unique Substrate Specificity", *Biochemistry*, 41(23): 7424-7434,2002.

Myette et al., "Expression in *Escherichia coli*, Purification and Kinetic Characterization of Human Heparan Sulfate 3-$O$-Sulfotransferase-1", *Biochemical and Biophysical Research Communications*, 290(4): 1206-1213, 2002.

Natke et al., "Heparinase Treatment of Bovine Smooth Muscle Cells Inhibits Fibroblast Growth Factor-2 Binding to Fibroblast Growth Factor Receptor but not FGF-2 Mediated Cellular Proliferation", *Angiogenesis*, 3: 249-257, 1999.

Nesheim et al., "Dependence of Antithrombin III and Thrombin Binding Stoichiometries and Catalytic Activity on the Molecular Weight of Affinity-purified Heparin", *The Journal of Biological Chemistry*, 261(7): 3214-3221, 1986.

Padera et al., "FGF-2/ Fibroblast Growth Factor Receptor/ Heparin-like Glycosaminoglycan Interactions: A Compensation Model for FGF-2 Signaling", *The FASEB Journal*, 13(13): 1677-1687, 1999.

Pixley et al., "Preparation of Highly Stable Antithrombin-sepharose and Utilization for the Fractionation of Heparin", *Thrombosis Research*, 26(2): 129-133, 1982.

Pojasek et al., "Biochemical Characterization of the Chondroitinase B Active Site", *The Journal of Biological Chemistry*, 277(34): 31179-31186, 2002.

Pojasek et al., "Recombinant Expression, Purification, and Kinetic Characterization of Chondroitinase AC and Chondroitinase B from *Flavobacterium heparinum*", *Biochemical and Biophysical Research Communications*, 286(2): 343-351, 2001.

Raman et al., "Identification of Structural Motifs and Amino Acids within the Structure of Human Heparan Sulfate 3-$O$-Sulfotransferase that Mediate Enzymatic Function", *Biochemical and Biophysical Research Communications*, 290(4): 1214-1219, 2002.

Raman et al., "The Heparin / Heparan Sulfate 2-*O*-Sulfatase from *Flavobacterium heparinum*: A Structural and Biochemical Study of the Enzyme Active Site and Saccharide Substrate Specificity", *The Journal of Biological Chemistry*, 278(14): 12167-12174, 2003.

Rhomberg et al., "Mass Spectrometric Sequencing of Heparin and Heparan Sulfate Using Partial Digestion with Heparinases", *45th Annual Conference of Mass Spectrometry Allied Topics*, p. 1026-1027, 1997. Abstract Only.

Rhomberg et al., "Mass Spectrometric and Capillary Electrophoretic Investigation of Heparin, Heparinases, and Related Compounds", *MIT (Department of Chemistry)*, 1998. Thesis.

Rudd et al., "Oligosaccharide Sequencing Technology", *Nature*, 388: 205-207, 1997.

Sasisekharan et al., "Roles of Heparan-sulphate Glycosaminoglycans in Cancer", *Nature Reviews*, 2: 521-528, 2002.

Shriver et al., "Emerging Views of Heparan Sulfate Glycosaminoglycan Structure / Activity Relationships Modulating Dynamic Biological Functions", *TCM*, 12(2): 71-77, 2002.

Sundaram et al., "Rational Design of Low-molecular Weight Heparins with Improved In vivo Activity", *PNAS*, 100(2): 651-656, 2003.

Taylor et al., "Protamine is an Inhibitor of Angiogenesis", *Nature*, 297: 307-312, 1982.

Wishart et al., "A Single Mutation Converts a Novel Phosphotyrosine Binding Domain into a Dual- specificity Phosphatase", *The Journal of Biological Chemistry*, 270(45): 26782-26785, 1995.

Witkowski et al., "Conversion of a β-Ketoacyl Synthase to a Malonyl Decarboxylase by Replacement of the Active-site Cysteine with Glutamine", *Biochemistry*, 38(36): 11643-11650, 1999.

Yamada et al., "Structural Studies on the Bacterial Lyase-resistant Tetrasaccharides Derived from the Antithrombin III-binding Site of Porcine Intestinal Heparin", *The Journal of Biological Chemistry*, 268(7): 4780-4787, 1993.

Yan et al., "Prime Numbers and the Amino Acid Code: Analogy in Coding Properties", *J. Theor. Biol.*, 151: 333-341, 1991.

Yoder et al., "New Domain Motif: The Structure of Pectate Lyase C, a Secreted Plant Virulence Factor", *Science*, 260:1503-1506, 1993.

Yoder et al., "Unusual Structural Features in the Parallel β-helix in Pectate Lyases", *Structure*, 1(4):241-251, 1993.

Zhang et al., "6-*O*-Sulfotransferase-1 Represents a Critical Enzyme in the Anticoagulant Heparan Sulfate Biosynthetic Pathway", *The Journal of Biological Chemistry*, 276(45): 42311-42321, 2001.

Alderman, C.P. et al., "Continuous Subcutaneous Heparin Infusion for Treatment of Trousseau's Syndrome", *The Annals of Pharmacotherapy*, Jul./Aug. 1995, pp. 710-713, vol. 29.

Bernstein, H. et al., "Immobilized Heparin Lyase System for Blood Deheparinization", *Methods in Enzymology*, 1988, pp. 515-529, vol. 137, Academic Press, Inc.

Cardin, A.D. et al., "Molecular Modeling of Protein-Glycosaminoglycan Interactions", *Arteriosclerosis*, Jan./Feb. 1989, pp. 21-32, vol. 9, No. 1.

Comfort, A.R. et al., "Immobilized Enzyme Cellulose Hollow Fibers: III. Physical Properties and In Vitro Biocompatibility", *Biotechnology and Bioengineering*, 1989, pp. 1383-1390, vol. 34, John Wiley & Sons, Inc.

Edwards, D.A. et al., "Large Porous Particles for Pulmonary Drug Delivery", *Science Reprint Series*, Jun. 20, 1997, pp. 1868-1871, vol. 276, American Association for the Advancement of Science.

Edwards, D.A. et al., "Recent advances in pulmonary drug delivery using large, porous inhaled particles", *Appl. Physoil.*, Aug. 1998, pp. 379-385, vol. 85, No. 2, American Physiological Society.

Enriquez-Harris, P. et al., "Growth factors and the extracellular matrix", *Meeting Report, Trends in Cell Biology*, 1994, 2 Pages.

Ernst, S. et al., "Direct evidence for a predominantly exolytic processive mechanism for depolymerization of heparin-like glycosaminoglycans by heparinase I", *Proc. Natl. Acad. Sci. USA*, Apr. 1998, pp. 4182-4187, vol. 95.

Feingold, D.S. et al., "Conformational aspects of the reaction mechanisms of polysaccharide lyases and epimerases", *FEB Letters*, Nov. 1987, pp. 207-211, vol. 223, No. 2, Elsevier Science Publishers B.V.

Godavarti, R. et al., "Heparinase I from *Flavobacterium heparinum*. Identification of a Critical Histidine Residue Essential for Catalysis as Probed by Chemical Modification and Site-Directed Mutagenesis", *Biochemistry*, 1996, pp. 6846-6852, vol. 35, No. 21, American Chemical Society.

Godavarti, R. et al., "Heparinase III for *Flavobacterium heparinum*: cloning and recombinant expression in *Escherichia coli*", *Biochem. Biophys. Res. Commun.*, Aug. 23, 1996, pp. 751-758, vol. 225, No. 3, Academic Press, Inc.

Godavarti, R. et al., "A comparative analysis of the primary sequences and characteristics of heparinases I, II, and III from *Flavobacterium heparinum*", *Biochem. Biophys. Res. Commun.*, Dec. 24, 1996, pp. 770- 777, vol. 229, No. 3, Academic Press, Inc.

Harenberg, J. et al., "Anticoagulant effects and tissue factor pathway inhibitor after intrapulmonary low- molecular-weight heparin", *Blood Coagulation and Fibrinolysis*, 1996, pp. 477-482, vol. 7, Rapid Science Publishers.

Hart, G.W., "Glycosylation", *Current Opinion in Cell Biology*, 1992, pp. 1017-1023, vol. 4.

Huang, J.N. et al., "Low-Molecular-Weight Heparins", *Hematology/Oncology Clinics of North America*, Dec. 1998, pp. 1251-1281, vol. 12, No. 6.

Jackson, R.L. et al., "Glycosaminoglycans: Molecular Properties, Protein Interactions, and Role in Physiological Processes", *Physiological Reviews*, Apr. 1991, pp. 481-539, vol. 71, No. 2, The American Physiological Society.

Kakkar, A.K. et al., "Venous thromboembolism and cancer", *Baillier's Clinical Haematology*, Sep. 1998, pp. 675-687, vol. 11, No. 3, Bailliere Tindall.

Kanabrocki, E.L. et al., "Heparin as a Therapy for Atherosclerosis: Preliminary Observations on the Intrapulmonary Administration of Low-Dose Heparin in the Morning Versus Evening Gauged by Its Effect on Blood Variables", *Chronobiology International*, 1991, pp. 210-233, vol. 8, No. 3, International Society of Chronobiology.

Kanabrocki, E.L. et al., "A Quest for the Relief of Atherosclerosis: Potential Role of Intrapulmonary Heparin—A Hypothesis", *Quarterly Journal of Medicine*, Apr. 1992, pp. 259-282, New Series 83, No. 300, Oxford University Press.

Kretsinger, R.H. et al., "Structure and Evolution of Calcium-Modulated Proteins", *CRC Critical Reviews in Biochemistry*, Jul. 1980, pp. 119-174, vol. 8, No. 2.

Leckband, D. et al., "An Approach for the Stable Immobilization of Proteins", *Biotechnology and Bioengineering*, 1991, pp. 227-237, vol. 37, John Wiley & Sons, Inc.

Linhardt, R.J. et al., "Polysaccharide Lyases", *Applied Biochemistry and Biotechnology*, 1986, pp. 135-176, vol. 12.

Linhardt, R.J. et al., "Examination of the Substrate Specificity of Heparin and Heparan Sulfate Lyases", *Biochemistry*, 1990, pp. 2611-2617, vol. 29, No. 10, American Chemical Society.

Linhardt, R.J. et al., "Production and Chemical Processing of Low Molecular Weight Heparins", *Seminars in Thrombosis and Hemostatis*, 1999, pp. 5-16, vol. 25, Suppl. No. 3, Thiemo Medical Publishers, Inc.

Liu, D. et al., "The Calcium-binding Sites of Heparinase I from *Flavobacterium heparinum* are Essential for Enzymatic Activity", *The Journal of Biological Chemistry*, Feb. 12, 1999, pp. 4089-4095, vol. 274, No. 7, The American Society for Biochemistry and Molecular Biology, Inc.

Liu, J. et al., "Heparan Sulfate D-Glucosaminyl 3-0-Sulfotransferase-3A Sulfates N-Unsubstituted Glucosamine Residues", *The Journal of Biological Chemistry*, Dec. 31, 1999, pp. 38155-38162, vol. 274, No. 53, The American Society for Biochemistry and Molecular Biology, Inc.

Lohse, D.L. et al., "Purification and Characterization of Heparin Lyases from *Flavobacterium heparinum*", *The Journal of Biological Chemistry*, Dec. 5, 1992, pp. 24347-24355, vol. 267, No. 34, The American Society for Biochemistry and Molecular Biology, Inc.

Lustig, F. et al., "Alternative Splicing Determines the Binding of Platelet-Derived Growth Factor (PDGF-AA) to Glycosaminoglycans", *Biochemistry*, 1996, pp. 12077-12085, vol. 35, No. 37, American Chemical Society.

Pojasek, K. et al., "Histidine 295 and histidine 510 are crucial for the enzymatic degradation of heparan sulfate by heparinase III", *Biochemistry*, Apr. 11, 2000, pp. 4012-4019, vol. 39, No. 14, American Chemistry Society.

Rhomberg, A.J. et al., "Mass spectrometric and capillary electrophoretic investigation of the enzymatic degradation of heparin-like glycosaminoglycans", *Proc. Natl. Acad. Sci. USA*, Apr. 1998, pp. 4176-4181, vol. 95.

Rhomberg, A.J. et al., "Mass spectrometric evidence for the enzymatic mechanism of the depolymerization of heparin-like glycosaminoglycans by heparinase II", *Proc. Natl. Acad. Sci. USA*, Oct. 1998, pp. 12232-12237, vol. 95.

Sasisekharan, R. et al., "Cloning and expression of heparinase I gene from *Flavobacterium heparinum*", *Proc. Natl. Acad. Sci. USA*, Apr. 1993, pp. 3660-3664, vol. 90, Applied Biological Sciences.

Sasisekharan, R. et al., "Heparinase inhibits neovascularization", *Proc. Natl. Acad. Sci. USA*, Feb. 1994, pp. 1524-1528, vol. 91.

Sasisekharan, R. et al., "Heparinase I from *Flavobacterium heparinum*: The Role of the Cysteine Residue in Catalysis as Probed by Chemical Modification and Site-Directed Mutagenesis", *Biochemistry*, 1995, pp. 14441-14448, vol. 34, No. 44, American Chemical Society.

Sasisekharan, R. et al., "Heparinase I from *Flavobacterium heparinum*, Mapping and Characterization of the Heparin Binding Domain", *The Journal of Biological Chemistry*, Feb. 9, 1996, pp. 3124-3131, vol. 271, No. 6, The American Society for Biochemistry and Molecular Biology, Inc.

Sasisekharan, R. et al., "Heparin and heparan sulfate: biosynthesis, structure and function", *Curr. Opin. Chem. Biol.*, Dec. 2000, pp. 626-631, vol. 4, No. 6, The American Society for Biochemistry and Molecular Biology, Inc.

Shriver, Z. et al., "Heparinase II from *Flavobacterium heparinum*, Role of Histidine Residues in Enzymatic Activity as Probed by Chemical Modification and Site-Directed Mutagenesis", *The Journal of Biological Chemistry*, Apr. 24, 1998, pp. 10160-10167, vol. 273, No. 17, The American Society for Biochemistry and Molecular Biology, Inc.

Shriver, Z. et al., "Heparinase II from *Flavobacterium heparinum*, Role of cysteine in Enzymatic Activity as Probed by Chemical Modification and Site-Directed Mutagenesis", *The Journal of Biological Chemistry*, Sep. 4, 1998, pp. 22904-22912, vol. 273, No. 36, The American Society for Biochemistry and Molecular Biology, Inc.

Shriver, Z. et al., "Biochemical Investigations and Mapping of the Calcium-binding Sites of Heparinase I from *Flavobacterium heparinum*", *The Journal of Biological Chemistry*, Feb. 12, 1999, pp. 4082-4088, vol. 274, No. 7, The American Society for Biochemistry and Molecular Biology, Inc.

Shriver, Z. et al., "Sequencing of 3-0 sulfate containing heparin decasaccharides with a partial antithrombin III binding site", *Proc. Natl. Acad. Sci. USA*, Sep. 12, 2000, pp. 10359-10364, vol. 97, No. 19.

Shriver, Z. et al., "Cleavage of the antithrombin III binding site in heparin by heparinases and its implication in the generation of low molecular weight heparin", *Proc. Natl. Acad. Sci. USA*, Sep. 12, 2000, pp. 10365-10370, vol. 97, No. 19.

Valentine, K.A. et al., "Low-Molecular-Weight Heparin Therapy and Mortality", *Seminars in Thrombosis and Hemostatis*, 1997, pp. 173-178, vol. 23, No. 2, Thieme Medical Publishers, Inc.

Venkataraman, G. et al., "Sequencing complex polysaccharides", *Science*, Oct. 15, 1999, pp. 537-542, vol. 286(5439).

Yang, V.C. et al., "Purification and Characterization of Heparinase from *Flavobacterium heparinum*", *The Journal of Biological Chemistry*, Feb. 10, 1985, pp. 1849-1857, vol. 260, No. 3, The American Society of Biological Chemists, Inc.

Zacharski, L.R. et al., "Blood Coagulation Activation in Cancer: Challenges for Cancer Treatment", Hamostaseologic,1995, pp. 14-20, vol. 15, F.K. Schattauer Verlagsgesellschaft mbH.

Basten et al., In vitro evaluation of synthetic heparin-like conjugates comprising different thrombin binding domains. Bioorg Med Chem Lett. May 19, 1998;8(10):1201-6. Abstract Only.

Bauer et al., Pharmazeutische Technologie, $3^{rd}$ Ed. 1991:251-2. German language reference.

Beales et al., The effect of a heparin analogue, ITF-5005, on diabetes incidence and insulitis in the non-obese diabetic mouse. Diabetes Res Clin Pract. Jul. 1993;21(1):5-9. Abstract Only.

Belford et al., Ability of different chemically modified heparins to potentiate the biological activity of heparin-binding growth factor 1: lack of correlation with growth factor binding. Biochemistry. Jul. 21, 1993;31(28):6498-503.

Ben-Jebria et al., Large porous particles for sustained protection from carbachol-induced bronchoconstriction in guinea pigs. Pharm Res. Apr. 1999;16(4):555-61.

Casu et al., Heparin-like compounds prepared by chemical modification of capsular polysaccharide from *E. coli* K5. Carbohydr Res. Oct. 17,1994;263(2):271-84. Abstract Only.

Desai et al., Structure elucidation of a novel acidic tetrasaccharide and hexasaccharide derived from a chemically modified heparin. Carbohydr Res. Mar. 17, 1993;241:249-59.

Gonzalez, Low-molecular-weight heparins for acute coronary syndromes: an emergency medicine perspective. Pharmacotherapy. Sep. 1999;19(9 Pt 2):155S-160S. Abstract Only.

Hunnius, Pharmazeutisches Wörterbuch, de Gruyter Verlag, $7^{th}$ Ed., 1994:26-7. German language reference.

Kibbe et al., Handbook of Pharmaceutical Excipients. American Pharmaceutical Association. Washington, D.C. 2000:102-9, 522-7.

Petitou et al., New synthetic heparin mimetics able to inhibit thrombin and factor Xa. Bioorg Med Chem Lett. Apr. 19, 1999;9(8):1155-60. Abstract Only.

Ruiz-Calero et al., Use of reversed polarity and a pressure gradient in the analysis of disaccharide composition of heparin by capillary electrophoresis. J Chromatogr A. Dec. 18, 1999;828(1-2):497-508. Abstract only.

Torngren et al., Conventional heparin and semisynthetic heparin analogue (SSHA) alteration of blood coagulation after embolic occlusion of human renal circulation. Thromb Res. Jul. 15, 1990;59(2):237-46. Abstract Only.

Wang et al., Inhalation of estradiol for sustained systemic delivery. J Aerosol Med. 1999 Spring; 12(1):27-36.

Kreitz, M.R. et al. (1997), "Controlled delivery of therapeutics from microporous membranes. II. In vitro degradation and release of heparin-loaded poly(D,L-lactide-co-glycolide)", *Biomaterials* 18:1645.

* cited by examiner

Figure 2

METHODS AND PRODUCTS RELATED TO PULMONARY DELIVERY OF POLYSACCHARIDES

RELATED APPLICATIONS

This application claims priority under 35 U.S.C. §119 from U.S. provisional application Ser. No. 60/241,559, filed Oct. 18, 2000, the entire contents of which is incorporated by reference.

FIELD OF THE INVENTION

The present invention relates to methods and products associated with pulmonary delivery of polysaccharides. In particular methods and products for delivering both unformulated and formulated polysaccharides are described.

BACKGROUND OF THE INVENTION

Recent advances in medicine have produced several alternative modes of drug delivery. Drugs which were previously only available in injectable forms, are now available in less invasive forms such as oral tablets or capsules, sustained release devices, and transdermal patches. Many of these advances, however, have occurred with protein based or small molecule drugs. Delivery of polysaccharides for therapeutic or prophylactic purposes is still associated with some problems.

Oral delivery of drugs is often preferred. The rapid metabolism of polysaccharides in the gastrointestinal tract, however, has prohibited their oral administration. Pulmonary delivery of drugs has also been proposed to be a preferred route of drug administration because of the large surface area of blood vessels in alveoli. The thin barrier between the rich capillary bed and the air coupled with the very high blood flow rate makes alveoli of lungs one of the most desirable drug delivery sites. Pulmonary delivery of protein based drugs has been quite successful. Investigators, however, have been trying for over 30 years to administer polysaccharides such as heparin by pulmonary delivery, with much less success. For instance, delivering heparin by conventional liquid aerosol spray or instillation only received limited success due to its poor penetration to the deep lung and resultant poor pharmacokinetics performance. An exceedingly high dose of heparin is required to generate meaningful pharmacological effects when inhaled as liquid heparin.

Natural polysaccharides such as heparin are polydisperse mixtures containing a large number of chains having different molecular weights (MWs) and as such the pharmacokinetics of these compounds are complicated. The anticoagulant response of heparin, for instance, increases disproportionately in intensity and duration as the dose increases. As a result, anticoagulant effect of heparin often has to be closely monitored to minimize the occurrence of potentially dangerous hemorrhage, which is the most common and major side effect of heparin. Since heparin is not a single chemical entity and its disposition is determined by a number of pathophysiologic factors, its pharmacokinetic parameters vary substantially among different individuals and thus require dose adjustment for each specific individual. The frequency of side effects is associated with the routes of administration. The risk is higher in intermittent (14.2%) and continuous (6.8%) infusion than the subcutaneous route (4.1%).

SUMMARY OF THE INVENTION

The invention relates to improved methods and products for delivering polysaccharides for prophylactic and therapeutic purposes. The invention is based in some aspects on the surprising discovery that pulmonary administration of polysaccharides in a dry aerosol form, in a formulated or unformulated form, results in an extremely rapid and efficient delivery of the polysaccharide locally and systemically. Many attempts have been made in the past to deliver polysaccharides such as heparin by inhalation. In general these attempts have been unsuccessful. It is well established that when heparin is delivered in a liquid aerosol, the amount of heparin that is absorbed in the blood is extremely low. It was discovered according to the invention that polysaccharides could be administered by pulmonary delivery in a dry aerosol with excellent results, including rapid absorption and good bioavailability, resulting in significant therapeutic benefits.

Thus, in some aspects, the invention is a method for delivering a polysaccharide to a subject in an unformulated dry powder. For instance, a method for producing a therapeutic effect by administering to a pulmonary tissue of a subject an unformulated dry polysaccharide particle in an effective amount for producing a therapeutic effect, wherein the unformulated dry polysaccharide particle has a mean geometric diameter of 1-500 microns, is provided.

In other aspects the invention is a method for delivering at least 5% and preferably at least 10% of a polysaccharide to the lower respiratory tract by administering to a pulmonary tissue of a subject an unformulated dry polysaccharide particle, wherein the unformulated dry polysaccharide particle has a mean geometric diameter of 1-500 microns, and wherein at least 5% or 10% of the polysaccharide administered is delivered to the lower respiratory tract.

In yet another aspect the invention is a method for systemically delivering a polysaccharide to a subject by administering to a pulmonary tissue of the subject an unformulated dry polysaccharide particle, wherein the unformulated dry polysaccharide particle has a mean geometric diameter of 1-500 microns.

The polysaccharide useful in the methods is any type of polysaccharide which has a prophylactic or therapeutic utility. In one embodiment the polysaccharide is a glycosaminoglycan, such as, for example, a heparin, a heparin sulfate, a low molecular weight heparin, a biotechnology derived heparin, a chemically modified heparin, a heparin mimetic (e.g., a monosaccharide, oligosaccharide or polysaccharide that has at least one heparin-like function such as AT-III binding), or an unfractionated heparin preparation.

Generally the unformulated dry polysaccharide particle has a mean geometric diameter of 1-500 microns, or any range of integers therebetween. In some embodiments the unformulated dry polysaccharide particle has a mean geometric diameter of 1-50, 1-200, 53-106, 1-5, 1-20, 20-53, 53-75, or 75-106 microns. In other embodiments the unformulated dry polysaccharide particle has a mean aerodynamic diameter of 1-5, 5-35, 1-35, 35-70, 35-75, or 1-50 microns. In yet other embodiments the unformulated dry polysaccharide has a tap density of 0.01-0.4 $g/cm^3$ or greater than 0.4 $g/cm^3$.

The prophylactic or therapeutic utility of the polysaccharide being delivered varies depending on the type of polysaccharide as well as the subject being treated. Some polysaccharides, for instance, are useful as vaccine antigens. These are generally used for prophylactic purposes, but, in some cases can be used therapeutically as well. Other polysaccharides have very diverse utilities, such as, the glycosaminoglycans, and in particular heparin-like-glycosaminoglycans.

Glycosaminoglycans have been established to be useful for treating and preventing coagulation disorders, thrombotic disorders, cardiovascular disease, vascular conditions, atherosclerosis, respiratory disorders, cancer, and angiogenic disorders.

Thus, in some embodiments the subject has or is at risk of a coagulation disorder and the therapeutic effect of the glycosaminoglycan is anti-coagulation or antithrombosis. In other embodiments the glycosaminoglycan is useful for treating cardiovascular disease, such as for instance, acute myocardial infarction, unstable angina, ischemic stroke, and atrial fibrillation, and vascular conditions, such as for instance, deep venous thrombosis, stroke, and pulmonary embolism. In other embodiments the subject is preparing to undergo, is undergoing or is recovering from a surgical procedure or the subject is undergoing a tissue or organ transplant. Surgical procedures include but are not limited to cardiac-pulmonary by-pass surgery, coronary revascularization surgery, orthopedic surgery, and prosthesis replacement surgery.

The subject in other embodiments has or is at risk of atherosclerosis, a respiratory disorder, a cancer or metastasis, an inflammatory disorder, an allergy, and/or an angiogenic disorder. Respiratory disorders include but are not limited to asthma, emphysema, adult respiratory distress syndrome (ARDS), and lung, kidney, heart gut, brain, skeletal muscle ischemial-reperfusion injury. Angiogenic disorders include but are not limited to neovascular disorders of the eye, osteoporosis, psoriasis, and arthritis.

In other embodiments the polysaccharide is a chondroitin sulfate, dermatan sulfate, hyaluronic acid, pectin or pectin derivative, oligosaccharide or pentasaccharide that binds to AT-III, laminarin, PI-88, sulfated chitin, or other animal-derived, plant-derived, microorganism-derived, natural, synthetic, or modified polysaccharide. Pectins and pectin derivatives are useful for anti-tumor applications.

In some embodiments when the polysaccharide is a glycosaminoglycan being administered for anticoagulant purposes, it is administered in an amount effective to produce a minimum therapeutic level of approximately 0.35 IU/ml antifactor Xa activity.

The unformulated dry polysaccharide may be self administered by the subject or it may be administered by another, such as a health care professional. For instance, the unformulated dry polysaccharide may be administered through a tracheal tube.

In other aspects, the invention is a composition consisting of unformulated dry glycosaminoglycan having a mean geometric diameter of 1-500 microns. In some embodiments the unformulated dry polysaccharide particle has a mean geometric diameter of 1-50, 1-200, 53-106, 1-5, 1-20, 20-53, 53-75, or 75-106 microns. In embodiments the unformulated dry polysaccharide particle has a mean aerodynamic diameter of 1-5, 5-35, 1-35, 35-70, 35-75, or 1-50 microns.

The glycosaminoglycan in some embodiments may be a heparin, a heparin sulfate, a low molecular weight heparin, a biotechnology derived heparin, a chemically modified or synthesized heparin, heparin mimetics and an unfractionated heparin preparation.

Optionally the composition may additionally include a formulated dry glycosaminoglycan preparation. The glycosaminoglycan of the formulated dry glycosaminoglycan preparation may also be a heparin, a heparin sulfate, a low molecular weight heparin, a biotechnology derived heparin, a chemically modified heparin, a heparin mimetic, and an unfractionated heparin preparation.

In some embodiments the glycosaminoglycan of the formulated dry preparation is the same as the glycosaminoglycan of the unformulated dry preparation and in other embodiments the glycosaminoglycan of the formulated dry preparation is different than the glycosaminoglycan of the unformulated dry preparation.

Optionally, the formulated dry glycosaminoglycan preparation includes a polymer to effect slow release of the glycosaminoglycan. Thus the glycosaminoglycan of the unformulated preparation will be released rapidly and the glycosaminoglycan of the formulated preparation will be released slowly over time. In some embodiments the polymer is selected from the group consisting of poly lactic acid (PLA), polyglycolic acid (PGA), poly (D,L, -lactic-co-glycolic acid) (PLGA), polyamides, polycarbonates, poly(ethylene oxide), polyvinyl compounds, poly vinyl ethers, polymers of acrylic and methacrylic acids, celluloses, and other polysaccharides. In other embodiments the formulated dry glycosaminoglycan preparation includes a surfactant, such as DPPC, polyoxethylene-9-; auryl ether; palmitic acid; oleic acid; sorbitan trioleate (Span 85); glycocholate; surfactin; poloxomer; sorbitan fatty acid; sorbitan trioleate; tyloxapol; and phopholipids.

A method for delivering a glycosaminoglycan to a subject by administering to a pulmonary tissue of a subject the above-described compositions is also disclosed according to the invention.

In other aspects the invention relates to methods of delivering either or both formulated and unformulated polysaccharides by pulmonary administration. Thus the invention in one aspect is a method of rapidly delivering a polysaccharide to a subject by administering a dry aerosol containing a polysaccharide to a pulmonary tissue of a subject in an effective amount to produce a peak plasma concentration of polysaccharide within three and preferably two hours.

In other aspects the invention is a method of rapidly delivering a polysaccharide to a subject by administering a dry aerosol containing a polysaccharide to a pulmonary tissue of a subject in an effective amount to produce a peak therapeutic activity of polysaccharide within three or preferably two hours. In some embodiments the dry aerosol containing a polysaccharide is administered in an effective amount to produce the peak concentration or activity of polysaccharide within one and one half hours. In other embodiments the dry aerosol containing a polysaccharide is administered in an effective amount to produce the peak concentration or activity of polysaccharide within one hour or preferably within a half hour.

The polysaccharide in some embodiments is a glycosaminoglycan. Glycosaminoglycans include but are not limited to low-molecular-weight heparin, heparin, heparin sulfate, biotechnology derived heparin, chemically modified heparin, heparin mimetic, and unfractionated heparin preparation.

In some embodiments the dry aerosol contains an unformulated dry polysaccharide and in other embodiments it contains a formulated dry polysaccharide preparation or some combination thereof. Optionally the dry aerosol contains a dry polysaccharide formulated in a surfactant, such as DPPC. The surfactant may optionally be coated on the particle surface or incorporated into the formulation.

In other embodiments additional molecules may optionally be administered. These include, for instance, proteins, peptides, nucleic acids (e.g., RNA, DNA, PNA, multiplexes of them (e.g.: triplex), and, small organic molecules).

The invention in another aspect relates to a method of rapidly delivering a polysaccharide to a subject by administering a dry aerosol containing a polysaccharide to a pulmonary tissue of a subject in an effective amount to deliver at least 5% of the polysaccharide to the blood within one hour.

In some embodiments at least 5% of the polysaccharide is detectable in the blood within one hour. In other embodiments at least 10%, 20%, 30%, 40%, 50%, 60%, 70%, 80%, or 90% of the polysaccharide is delivered to or detectable in the blood within one hour.

In other aspects the invention is a method for producing a rapid therapeutic effect by administering a dry aerosol containing a polysaccharide to a pulmonary tissue of a subject in an effective amount for producing a therapeutic effect within 1 hour of administration. In some embodiments the dry aerosol is administered in an effective amount for producing a therapeutic effect within 15 minutes of administration. In yet other embodiments the dry aerosol is administered in an effective amount for producing a therapeutic effect within 10 minutes of administration.

The invention in another aspect is a composition comprising a dry aerosol formulation of particles containing a heparin-like glycosaminoglycan, wherein the particles have a mean geometric diameter of greater than 30 microns. In some embodiments the particles are spherical and in other embodiments the particles are non-spherical. In yet other embodiments the particles are porous and in other embodiments the particles are non-porous.

A composition of a dry aerosol formulation of particles containing a heparin-like glycosaminoglycan, wherein the particles have a mean aerodynamic diameter of greater than 5 microns is provided according to another aspect of the invention.

In another aspect the invention relates to a composition of a dry aerosol formulation of particles containing a heparin-like glycosaminoglycan, wherein the particles have a tap density of greater than 0.4 g/cm$^3$.

Kits are provided according to yet other aspects of the invention. The kit is a kit for administering a dry aerosol containing a polysaccharide to the respiratory tract of a subject and includes an inhalation apparatus, a polysaccharide dry aerosol particle preparation and a detection system. The polysaccharide dry aerosol particle is formulated to release at least 5% of the polysaccharide within three or preferably two hours.

In one embodiment of the kit, the polysaccharide is a glycosaminoglycan, such as, a low-molecular-weight heparin, heparin, heparin sulfate, biotechnology derived heparin, chemically modified heparin, heparin mimetic and unfractionated heparin preparation.

The dry aerosol polysaccharide may be a formulated or unformulated polysaccharide particle preparation. The dry polysaccharide particle may have a mean geometric diameter of 1-500 microns, or any range of integers therebetween. In some embodiments the particle has a mean geometric diameter of 1-50, 1-200, 53-106, 1-5, 1-20, 20-53, 53-75, or 75-106 microns. In other embodiments the unformulated dry polysaccharide particle has a mean aerodynamic diameter of 1-5, 5-35, 1-35, 35-70, 35-75, or 1-50 microns.

According to other aspects of the invention a composition including both a formulated dry polysaccharide preparation and an unformulated dry polysaccharide preparation is provided. The polysaccharide may optionally be a glycosaminoglycan. Glycosaminoglycans include but are not limited to a heparin, a heparin sulfate, a low molecular weight heparin, a biotechnology derived heparin, a chemically modified heparin, a heparin mimetic, and an unfractionated heparin preparation.

In some embodiments, the polysaccharide of the formulated dry preparation is the same as the polysaccharide of the unformulated dry preparation and in other embodiments the polysaccharide of the formulated dry preparation is different than the polysaccharide of the unformulated dry preparation.

Optionally, the formulated dry polysaccharide preparation includes a polymer to effect slow release of the polysaccharide. Thus the polysaccharide of the unformulated preparation will be released rapidly and the polysaccharide of the formulated preparation will be released slowly over time. In some embodiments the polymer may be PLA, PGA, or PLGA. In other embodiments the formulated dry polysaccharide preparation includes a surfactant, such as DPPC.

In some embodiments the ratio of unformulated preparation to formulated preparation is 90:10, 70:30, 50:50, 30:70, or 10:90.

In other aspects the invention is a method for delivering a polysaccharide to a subject by administering to a pulmonary tissue of the subject the above described composition, e.g., a dry aerosol formulation comprising an unformulated dry glycosaminoglycan preparation and a formulated dry glycosaminoglycan preparation to deliver the polysaccharide to the subject.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 2 is a set of graphs depicting the pharmacokinetics of 100% unformulated ardeparin particles in rabbits: a) the pharmacokinetics of anti-Xa activity of unformulated ardeparin of different particle size ranges in rabbits at 600 IU/kg. b) the pharmacokinetics of unformulated ardeparin is compared to s.c. administration at 600 IU/kg. c) comparison of pharmacokinetics between 600 and 300 IU/kg doses for unformulated ardeparin particle of 1-20 μm size in rabbits. d) comparison of pharmacokinetics between 600 and 300 IU/kg doses for unformulated ardeparin particles of 1-53 μm size. e) comparison of pharmacokinetics between s.c. administered ardeparin and dry unformulated ardeparin of different size ranges at 300 IU/kg. f) results of lavage study after inhalation of dry unformulated ardeparin of 1-53 μm size. The total amount of ardeparin in the lavage fluid and plasma was determined by anti-Xa assay. g) lavage study results of dry unformulated ardeparin of 1-53 μm size. The total amount of ardeparin in the lavage fluid and plasma was determined by anti-Xa assay.

DETAILED DESCRIPTION

Figure 1:
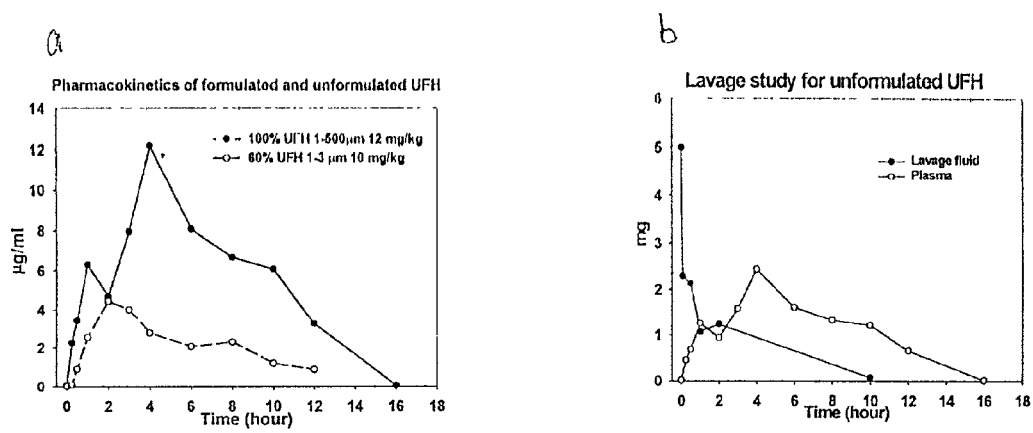
FIG. 1 is a set of graphs depicting the pharmacokinetics of UFH particles after inhalation: a) pharmacokinetics of UFH as unformulated dry powder (1-500 μm)(12 mg/kg) or formulated nonporous small particles (1-3 μm) with DPPC as excipient (60% UFH 40% DPPC) (10 mg/kg) in rats. b) lavage study of unformulated UFH in rats at 12 mg/kg. The amount of UFH in lavage fluid and plasma were determined by whole blood clotting assay method. The total amount of UFH found in lavage fluid at indicated time points was compared to the total amount of ardeparin in rat circulation at the corresponding time points. 15 ml plasma volume as used for converting concentration to total amount of UFH in circulation.

In general, intrapulmonary delivery of polysaccharides has met with very little success. The prior art techniques for intrapulmonary delivery have involved administration in the form of a liquid aerosol or intratracheal liquid instillation. Whether given as liquid aerosol or intratracheal liquid instillation, the bioavailability of polysaccharides such as heparin or LMWH delivered by an intrapulmonary route is consistently less than 10% of that achieved by s.c. (subcutaneous) or i.v. (intravenous) administration. When delivered as liquid heparin aerosol, the majority of heparin is trapped in the upper airways and only less than 10% of the delivered dose reaches the deep lung. Thus extremely high doses must be administered to achieve any therapeutic result. If heparin is administered at the same doses as that which is ordinarily used for s.c. or i.v. administration, no detectable heparin is found in the blood circulation after pulmonary delivery. An 8-10 times higher dose of heparin is required for intrapulmonary heparin to provide a similar heparin concentration in the blood circulation as that which is achieved with s.c. administration. Additionally the rate of absorption of heparin from the lung after intrapulmonary delivery of liquid heparin is much slower than that of s.c. administration. $t_{max}$ (the time when peak activity is reached) is typically observed 5 hours after intrapulmonary delivery. Substantial amounts of heparin have been observed to be remaining in the lung many hours after inhalation. Further, there has been no close dose-response relationship observed after intrapulmonary delivery of heparin. Considerable variations in the pharmacokinetics of intrapulmonary heparin have been reported, suggesting that this route of delivery may be dangerous because of the risk of heparin associated side effects.

There are several problems associated with pulmonary delivery of polysaccharides. Firstly, the presence of multiple membrane structures which separate the upper respiratory tract from the capillary circulation can lead to poor absorption. These lipid membrane structures are impermeable to hydrophilic macromolecules such as heparin and low molecular heparin which are highly negatively charged polymers. Delivery routes such as s.c. administration allow the polysaccharide to directly contact capillary vessels and thus be immediately absorbed. Pulmonary delivery methods also result in a large proportion of the drug being trapped in the trachea or upper respiratory tract.

It was unexpectedly discovered according to the invention that intrapulmonary administration of polysaccharides using a dry aerosol particle preparation resulted in excellent absorption and bioavailability, producing significant therapeutic results in vivo. Even more surprising, it was discovered that the dry aerosol particles did not even need to be formulated to produce these results. It has been well documented in the prior art that when proteins are administered as dry powder, the particles undergo two different fates. The particles either become trapped in the upper respiratory tract or are delivered to the lower respiratory tract or in some cases the deep lung. In the upper respiratory tract, ciliated epithelia contribute to a process referred to as the "mucosiliary escalator" in which particles are swept from the airways toward the mouth. In the deep lungs, alveolar macrophages phagocytosize the particles soon after their deposition. Small particles (diameter<5 μM) get phagocytosed to a higher degree than larger particles. The human lungs can remove or rapidly degrade deposited aerosols over periods ranging from minutes to hours. As the diameter of the particle increases, there is increasingly less phagocytosis by macrophages. However, increasing the particle size also minimizes the probability of particles (possessing standard mass density) entering the airways and acini due to excessive deposition in the oropharyngeal or nasal regions (upper respiratory tract). Thus, the large particles (diameter>5 μM) are known to get deposited excessively in the upper airways.

As a result of these teachings it is generally believed in the art that if a protein has to be delivered as a dry powder via pulmonary delivery, the protein must be formulated in a certain way to achieve maximal therapeutic benefit. For example, if a protein is formulated into dry particles which are made to be aerodynamically light, it can be delivered formulated with a surfactant via pulmonary delivery (U.S. Pat. No. 5,855,913). It was discovered surprisingly according to the invention that delivery of polysaccharides can be accomplished without adhering to these teachings. Polysaccharides behave in a way that is totally different from that predicted for an unformulated protein or other macromolecule. The data described in the Examples show that polysaccharides can be delivered via pulmonary inhalation, and that this process is independent of the size of the particle (within a broad range), texture, porosity, density, shape, and the presence or absence of additives.

The polysaccharides can be significantly absorbed as dry aerosol particles of defined sizes with or without excipients. Thus, a "dry aerosol containing a polysaccharide" encompasses both unformulated dry aerosol polysaccharide particles or preparations and formulated dry aerosol polysaccharide particles or preparations. An "unformulated dry aerosol polysaccharide particle or preparation" as used herein refers to a composition which is composed of a polysaccharide in the form of dry particles having a mean geometric diameter of 1-500 microns and which does not include a carrier or other excipient to enhance delivery or result in slow release. The unformulated dry aerosol polysaccharide particle may include non-essential agents which are not expected to influence the delivery or absorption of the polysaccharide. Materials which are known to influence polysaccharide release or absorption are polymeric materials and surfactants. Thus, both of these materials may be found in the formulated particles but not in the unformulated particles. The unformulated particles, however, may include compounds other than polymers (except for polysaccharides) and surfactants, as long as the particle includes at least one therapeutically active polysaccharide. These include, for instance, but are not limited to, proteins, nucleic acids, small organic or inorganic molecules, carriers that do not have slow release properties, preservatives, etc.

The unformulated (as well as the formulated) polysaccharide particles may include a single polysaccharide or multiple polysaccharides. Thus, the particles may include only one polysaccharide, more than one polysaccharide but only one polysaccharide which has a therapeutic activity, or more than one polysaccharide having a therapeutic activity.

A set of particles having a "mean geometric diameter of 1-500 microns" is a set of particles having at least 50% of the particles falling within the size range of 1-500 microns or any range of integer numbers falling within 1-500 microns. The mean geometric diameter can be determined by one of skill in the art using routine methods. For instance, mean geometric diameter can be established by scanning electron microscopy (SEM) or atomic force microscopy (AFM), which can be use to determine particle size, porosity and surface texture, as well as a coulter multisizer II (Coulter Electronics, Luton, Beds, England). In some embodiments the particles have a geometric size distribution of 1-250, 1-100, 1-50, 5-200, 10-500, 10-250, 10-100, 100-200, 100-150, 53-106, 1-5, 1-20, 20-53, 53-75, or 75-106 microns.

Unformulated dry aerosol particles can be prepared by any means known in the art for generating particles. One method for preparing the particles involves obtaining a dry pure preparation of the polysaccharide and grinding it to produce particles, optionally coupled with a step for selecting particles of a particular size range. Examples of this type of method are provided in the examples below. For instance, the polysaccharide can be ground into particles using a coffee grinder and then separated by size by using sieves of different mesh sizes. Other methods include single or double emulsion solvent-evaporation procedures and spray drying. Particles of specific sizes can be generated by cryogrinding. This is accomplished by cooling the particles to a very low temperature, such as −190° C., e.g., using liquid nitrogen, and then grinding the particles. Additionally, polysaccharide may be dissolved in a suitable solvent (e.g., water and a volatile organic solvent like methylene chloride) and then nebulized (i.e., passing it through a small orifice at high pressure). The solvent is then rapidly removed at a high temperature and the particles collected. An electrospray injector can be used for this purpose.

In addition to the mean geometric diameter the particles may have a specific range of aerodynamic diameters. In one embodiment the particles have a mean aerodynamic diameter of 1-50 microns. A "mean aerodynamic diameter" refers to the diameter that a particle appears to possess on the basis of its in-flight speed, where it is assumed to be spherical and to possess a mass density of 1 $g/cm^3$. The geometric diameter of a spherical particle possessing unit mass density (1 $g/cm^3$) is equivalent to its aerodynamic diameter. The aerodynamic diameter ($d_{aer}$) relates to a particle's geometric diameter (d) and mass density ($\rho$) with the function: $d_{aer}=d\rho^{1/2}$. In some embodiments the particles have a mean aerodynamic diameter of 1-5, 1-35, 1-75, 35-75, or 5-35 microns.

The polysaccharide particles with sizes ranging from 1-500 µm, porous or non-porous, spherical or non-spherical, light or heavy were associated with significant absorption profiles. Although the prior art has taught that these features are critical for promoting delivery of the particles to the deep lung, the data of the instant invention demonstrates that these properties are not critical for delivery to the deep lung. Thus the dry unformulated particles may have any physical properties, such as porosity or shape. The porosity and shape of the particle influence the aerodynamic properties of the particle. In some embodiments the particles may be aerodynamically light, but in other embodiments they may be heavy. The aerodynamic weight of the particle can be measured in terms of tap density. A particle that is aerodynamically light has a tap density of less than 0.4 $g/cm^3$ and preferably has a tap density in the range of 0.01 $g/cm^3$-0.4 $g/cm^3$. A particle that is aerodynamically heavy has a tap density of greater than 0.4 $g/cm^3$. Tap density refers to the mass density of the particle, which is calculated as the mass of the particle divided by the minimum sphere volume within which it can be enclosed. A measurement of tap density may be obtained using equipment such as a GeoPyc™ (Micrometrics Instrument Corp., Georgia).

The unformulated polysaccharide particles showed unique pharmacokinetics featuring an extremely rapid absorption rate and a comparable elimination rate to that of s.c. administration. The addition of excipients such as DPPC to the particles did not appear to alter the pharmacokinetic profiles significantly. Thus, the invention also encompasses the use of formulated dry aerosol polysaccharide particles. A "formulated dry aerosol polysaccharide particle or preparation" as used herein refers to a composition which is composed of a polysaccharide in the form of dry particles having a mean geometric diameter of 1-500 microns and which further includes a carrier or other excipient to enhance delivery or achieve slow release of the polysaccharide. Similar to the unformulated polysaccharide particles, the porosity and shape were not critical. Particles that were porous or non-porous, spherical or non-spherical, light or heavy were associated with significant absorption profiles. In one embodiment the formulated particles are those having the properties described in U.S. Pat. Nos. 5,855,913 and 5,985,309. These formulated dry particles are aerodynamically light and have a mean geometric diameter of 5-30 microns, a tap density of less than 0.4 $g/cm^3$ and an aerodynamic diameter of 1-5 microns. In other embodiments the formulated dry particles are those having different properties than those described in U.S. Pat. Nos. 5,855,913 and 5,985,309. For instance, it is possible that the formulated particles of the invention have a mean geometric diameter of 1-5 or 30-500 microns, a tap density of greater than 0.4 $g/cm^3$ and/or an aerodynamic diameter of 5-75 microns.

The formulated particles include at least one carrier or excipient. In one embodiment the excipient is a surfactant. A "surfactant" as used herein refers to a compound having a hydrophilic and lipophilic moiety, which promotes absorption of a drug by interacting with an interface between two immiscible phases. Surfactants are useful in the dry particles for several reasons, e.g., reduction of particle agglomeration, reduction of macrophage phagocytosis, etc. When coupled with lung surfactant, a more efficient absorption of polysaccharides can be achieved because surfactants, such as DPPC, will greatly facilitate diffusion of polysaccharides, such as heparin across the membrane surface of the alveoli by disguising the hydrophilic, charged groups of the heparin polymer. Surfactants are well known in the art and include but are not limited to phosphoglycerides, e.g., phosphatidylcholines, L-alpha-phosphatidylcholine dipalmitoyl (DPPC) and diphosphatidyl glycerol (DPPG); hexadecanol; fatty acids; polyethylene glycol (PEG); polyoxyethylene-9-; auryl ether; palmitic acid; oleic acid; sorbitan trioleate (Span 85); glycocholate; surfactin; poloxomer; sorbitan fatty acid ester; sorbitan trioleate; tyloxapol; phospholipids. The surfactant may be incorporated within the particle or it may be coated on the surface of the particle.

Controlled release of polysaccharide can also be achieved with appropriate excipient materials that are biocompatible and biodegradable. These polymeric materials which effect slow release of the polysaccharide may be any suitable polymeric material for generating particles, including, but not limited to, nonbioerodable/non-biodegradable and bioerodable/biodegradable polymers. Such polymers have been described in great detail in the prior art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, poly (methyl methacrylate), poly (ethylmethacrylate), poly(butylmethacrylate), poly(isobutylmethacrylate), poly(hexlmethacrylate), poly (isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride polystyrene, polyvinylpryrrolidone, hyaluronic acid, and chondroitin sulfate.

Examples of preferred non-biodegradable polymers include ethylene vinyl acetate, poly(meth) acrylic acid, polyamides, copolymers and mixtures thereof.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly (hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. The most preferred polymers are polyesters, polyanhydrides, polystyrenes and blends thereof.

In some instances, the invention encompasses a combination of formulated and unformulated polysaccharides. The combination may contain any ratio or proportion of formulated:unformulated preparation. For instance, the combination may include a ratio of 10:90, 20:80, 30:70, 40:60; 50:50; 60:40, 70:30, 80:20, or 90:10. When the ratio is 50:50, the actual amount of polysaccharide in the formulated portion of the combination may be less than the actual amount of polysaccharide in the unformulated portion because the formulation includes excipients which account for some of the mass of the formulated particles. The relative amounts may also be calculated as a relative ratio of formulated:unformulated particles. The relative ratios of formulated:unformulated particles include, but are not limited to, 10:90, 20:80, 30:70, 40:60, 50:50, 60:40, 70:30, 80:20, and 90:10. When the relative ratio of the combination preparation is 50:50, the preparation includes an equivalent actual amount of polysaccharide in the preparation.

The type of polysaccharide in the two components of the combination preparation may be the same or different. Thus, the polysaccharide that is in the formulated preparation may be the same type of polysaccharide that is in the unformulated preparation, i.e., both may contain LMWH. Alternatively, the type of polysaccharide may be different. For example, the unformulated polysaccharide preparation may be LMWH and the formulated polysaccharide preparation may be UFH.

The dry aerosol particles of the invention are administered by inhalation to pulmonary tissue. The term "pulmonary tissue" as used herein refers to any tissue of the respiratory tract and includes both the upper and lower respiratory tract, except where otherwise indicated. The particles may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges for use in an inhaler or insufflator may be formulated containing a powder mix of the polysaccharide and a suitable powder base such as lactose or starch, if the particle is a formulated particle. In addition to the formulated or unformulated particles administered, other materials such as 100% DPPC or other surfactant particles can be mixed in the dry aerosol particles to promote the delivery and dispersion of the dry formulated or unformulated particles. These are separate and distinct from the formulated or unformulated particles, but are optionally included to enhance some aspect of the delivery process.

The dry aerosol particles when administer are rapidly absorbed and can produce a rapid local or systemic therapeutic result. A local therapeutic effect refers to a biologic effect that occurs to the lung tissue. For instance, when the polysaccharide is a heparin, it may be desirable to produce a local effect for the treatment of a respiratory disease. A systemic effect refers to a biologic effect that occurs outside of the lung tissue, e.g., in the blood. It has been discovered that the peak activity of the delivered polysaccharide can be achieved within 3 hours and preferably within two hours. In some embodiments the peak activity can be achieved even more quickly, e.g., within one half hour or even within ten minutes. The surprisingly fast absorption of heparin, in particular, after inhalation as a dry aerosolized particle is believed to be extremely valuable in management of clinical conditions where a fast convenient non-invasive administration is desired. Heparin particles, especially 100% heparin (UFH and LMWH) particles, can be used in acute coronary syndrome such as unstable angina to prevent the development of MI or death. Presently, acute coronary syndrome is being treated either with i.v. UFH or s.c. administered LMWHs. Inhaled heparin particles will allow a rapid anticoagulation/ antithrombosis state in the blood which cannot be achieved with s.c. administration of LMWHs. Both i.v. UFH and s.c. LMWHs are being used for this purpose. The rapid absorption of heparin after inhalation can be combined with subsequent s.c. administration of LMWHs to improve the efficiency of antithrombotic/anticoagulation treatment. Alternatively, heparin particles formulated for longer biological half-life can be used as an alternative for s.c. administration of LMWHs. Similar regimens can also be adopted for use of heparin in cerebral vascular diseases such as stroke, which require immediate early intervention. These and other therapeutic uses are described in more detail above.

In one embodiment, the polysaccharide is delivered in an amount such that 5% of the polysaccharide is delivered to the lower respiratory tract or the deep lung. Although not being bound by a mechanism, it is believed that the methods for pulmonary delivery of polysaccharides have been successful because the methods result in efficient and rapid delivery to the lower respiratory tract or deep lung alveolar surface. Deep lung has the richest capillary network found in an organ in the human body, and the respiratory membrane separate capillary lumen from alveolar air space is very thin ($\leq 6$ μm) and extremely permissible. In addition, the liquid layer lining the alveolar surface is rich in lung surfactants. In other embodiments at least 10%, 20%, 30%, 40%, 50%, or 60% is delivered to the lower respiratory tract or to the deep lung. Delivery to either or both of these tissues results in efficient absorption of the polysaccharide and high bioavailability.

The amount of polysaccharide delivered to the lower respiratory tract or deep lung can be determined using routine methods. For instance, in a test system, lavage of animal lungs at indicated time intervals after inhalation can be used to determine the amount of heparin delivered to the lower respiratory tract. This data can be correlated to that amount which would occur in humans or animals being treated. Alternatively, a label, such as a radioactive or fluorescent label can be attached to the polysaccharide and used to determine the distribution of inhaled polysaccharide. The amount of polysaccharide delivered to the lower respiratory tract or deep lung also can be determined as the amount of therapeutic effect resulting from the presence of the polysaccharide in the lower respiratory tract or deep lung or in the region where the biological activity is occurring, e.g., the blood, or the blood plasma concentration of the polysaccharide. The type of parameter used to assess the effectivity of the delivery will vary depending on a variety of factors including the type of subject, the type of equipment available, and the disorder being treated or prevented. The peak plasma concentration of a polysaccharide can be determined by measuring the level of polysaccharide present in the blood over time and determining when the peak level of concentration is reached. The amount of a therapeutic effect or a peak plasma activity can be identified using routine assays. The type of these effects will depend on the therapeutic parameter being assessed. For instance, if the polysaccharide is administered in order to prevent coagulation the amount of inhibition of factor Xa activity can be assessed. It is known that a minimum therapeutic level of heparin-like glycosaminoglycan for producing therapeutic anticoagulant effect is approximately 0.35 IU/ml anti-factor Xa activity. HLGAGs are also useful for inhibiting enzymatic activity, such as human leukocyte elastase. In general, the IC50 of HLGAGs on human leukocyte elastase ranges from 1 ng/ml to 50 microgram/mil. Alternatively, the $A_i$ values of HLGAGs ranges from 10 nm to 10 μM. In other instances, when the polysaccharide is a polysaccharide isolated from *phellinus linteus*, the biological activity which can be assessed includes both cell-mediated immunity and humoral immunity. Thus, the level of cell-mediated immunity or antibody production may be measured in order to characterize the therapeutic effect of peak biological activity of these compounds. Other assays are well known to those of ordinary skill in the art for each of the different polysaccharides.

Thus, the invention relates to intrapulmonary administration of polysaccharides. A "polysaccharide" is a polymer composed of monosaccharides linked to one another. In many polysaccharides the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide). Polysaccharides include but are not limited to heparin-like glycosaminoglycans, chondroitin sulfate, hyaluronic acid and derivatives or analogs thereof, chitin in derivatives and analogs thereof, e.g., 6-0-sulfated carboxymethyl chitin, immunogenic polysaccharides isolated from *phellinus linteus*, PI-88 (a mixture of highly sulfated oligosaccharide derived from the sulfation of phosphomannum which is purified from the high molecular weight core produced by fermentation of the yeast *pichia holstii*) and its derivatives and analogs, polysaccharide antigens for vaccines, and calcium spirulan (Ca-SP, isolated from blue-green algae, *spirulina platensis*) and derivatives and analogs thereof.

The methods taught herein are sometimes described with reference to heparin-like glycosaminoglycans (HLGAGs) but the properties taught herein can be extended to other polysaccharides, and unless a claim specifies otherwise the claims encompass any polysaccharides having a therapeutic utility. As used herein the terms "HLGAG" and "glycosaminoglycans" are used interchangeably to refer to a family of molecules having heparin like structures and properties. These molecules include but are not limited to low molecular weight heparin (LMWH), heparin, biotechnologically prepared heparin, chemically modified heparin, synthetic heparin, heparin mimetics and heparin sulfate. The term "biotechnological heparin" encompasses heparin that is prepared from natural sources of polysaccharides which have been chemically modified and is described in Razi et al., Bioche. J. 1995 Jul. 15; 309 (Pt 2): 465-72. Chemically modified heparin is described in Yates et al., Carbohydrate Res (1996) Nov. 20; 294:15-27, and is known to those of skill in the art. Synthetic heparin is well known to those of skill in the art and is described in Petitou, M. et al., Bioorg Med Chem Lett. (1999) Apr. 19; 9(8):1161-6 and Vlodavsky et al., Int. J. Cancer, 1999, 83:424-431. Heparan Sulfate refers to a glycosaminoglycan containing a disaccharide repeat unit similar to heparin, but which has more N-acetyl groups and fewer N- and O-sulfate groups. Heparin mimetics are monosaccharides (e.g., sucralfate), oligosaccharides, or polysaccharides having at least one biological activity of heparin (i.e., anticoagulation, inhibition of cancer, treatment of lung disorders, etc.). Preferably these molecules are highly sulfated. Heparin mimetics may be naturally occurring, synthetic or chemically modified. (Barchi, J. J., Curr. Pharm. Des., 2000, March, 6(4):485-501).

LMWH as used herein refers to a heparin preparation having a molecular weight of about 3,000 daltons to about 8,000 daltons.

Several LMWH preparations are commercially available, but, LMWHs can also be prepared from heparin, using e.g., HLGAG degrading enzymes. HLGAG degrading enzymes include but are not limited to heparinase-I, heparinase-II, heparinase-III, D-glucuronidase and L-iduronidase. The three heparinases from *Flavobacterium heparinum* are enzymatic tools that have been used for the generation of LMWH (5,000-8,000 Da) and ultra-low molecular weight heparin (~3,000 Da). Heparinase I cleaves highly sulfated regions of HLGAGs at 2-O sulfated uronic acids, whereas heparinase II has a broader substrate specificity and cleaves glycosidic linkages containing both 2-O sulfated and nonsulfated uronic acids (Ernst, S., Langer, R., Cooney, C. L. & Sasisekharan, R. (1995) *Crit Rev Biochem Mol Biol* 30, 387-444). Heparinase III, as opposed to heparinase I, cleaves primarily undersulfated regions of HLGAGs, viz., glycosidic linkages containing a nonsulfated uronic acid (Ernst, S., Langer, R., Cooney, C. L. & Sasisekharan, R. (1995) *Crit Rev Biochem Mol Biol* 30, 387-444). Commercially available LMWH include, but are not limited to, enoxaparin (brand name Lovenox; clexane by Rhone-Poulenc Rorer), dalteparin (Fragmin, Pharmacia and Upjohn), certoparin (Sandobarin, Novartis), ardeparin (Normiflo, Wyeth Lederle), nadroparin (Fraxiparine, Sanofi-Winthrop), pharnaparin (Fluxum, Wassermann), reviparin (Clivarin, Knoll AG), and tinzaparin (Innohep, Leo Laboratories, Logiparin, Novo Nordisk).

The compositions may be administered therapeutically to a subject. As used herein, a subject is a vertebrate such as a human, non-human primate, cow, horse, pig sheep, goat, dog, cat, or rodent.

HLGAGs have many therapeutic utilities. The HLGAG compositions of the invention can be used for the treatment of any type of condition in which HLGAG therapy has been identified as a useful therapy. Thus, the invention is useful in a variety of in vitro, in vivo and ex vivo methods in which HLGAG therapies are useful. For instance, it is known that HLGAG compositions are useful for preventing and treating coagulation, angiogenesis, thrombotic disorders, cardiovascular disease, vascular conditions, atherosclerosis, respiratory disorders, circulatory shock and related disorders, Alzheimer's disease, as well as inhibiting cancer cell growth and metastasis. Each of these disorders is well-known in the art and is described, for instance, in *Harrison's Principles of Internal Medicine* (McGraw Hill, Inc., New York), which is incorporated by reference. The use of HLGAG compositions in various therapeutic methods is described and summarized in Huang, J. and Shimamura, A., Coagulation Disorders, 12, 1251-1281 (1998).

Thus, the HLGAG preparations are useful for treating or preventing disorders associated with coagulation. A "disease associated with coagulation" as used herein refers to a condition characterized by local inflammation resulting from an interruption in the blood supply to a tissue due to a blockage of the blood vessel responsible for supplying blood to the tissue such as is seen for myocardial or cerebral infarction. Coagulation disorders include, but are not limited to, cardiovascular disease and vascular conditions such as cerebral ischemia.

The methods of the invention are useful for treating cardiovascular disease. Cardiovascular diseases include, but are not limited to, acute myocardial infarction, unstable angina, and atrial fibrillation. Myocardial infarction is a disease state which occurs with an abrupt decrease in coronary blood flow that follows a thrombotic occlusion of a coronary artery previously narrowed by atherosclerosis. Such injury may be produced or facilitated by factors such as cigarette smoking, hypertension, and lipid accumulation. Acute angina is due to transient myocardial ischemia. This disorder is usually associated with a heaviness, pressure, squeezing, smothering, or choking feeling below the sternum. Episodes are usually caused by exertion or emotion, but can occur at rest.

Atrial fibrillation is a common form of arrhythmia generally arising as a result of emotional stress or following surgery, exercise, or acute alcoholic intoxication. Persistent forms of atrial fibrillation generally occur in patients with cardiovascular disease. Atrial fibrillation is characterized by disorganized atrial activity without discrete P waves on the surface ECG.

The compounds of the invention can be used for the treatment of cardiovascular disorders alone or in combination with other therapeutic agents for reducing the risk of a cardiovascular disease or for treating the cardiovascular disease. Other therapeutic agents include, but are not limited to, anti-inflammatory agents, anti-thrombotic agents, anti-platelet agents, fibrinolytic agents, lipid reducing agents, direct thrombin inhibitors, and glycoprotein IIb/IIIa receptor inhibitors.

Anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

Lipid reducing agents include gemfibrozil, cholystyramine, colestipol, nicotinic acid, probucol lovastatin, fluvastatin, simvastatin, atorvastatin, pravastatin, cirivastatin.

Glycoprotein IIb/IIIa receptor Inhibitors are both antibodies and non-antibodies, and include but are not limited to ReoPro (abcixamab), lamifiban, tirofiban.

Anti-thrombotic agents and anti-platelet agents are described in more detail below.

The HLGAG preparations are also useful for treating vascular conditions. Vascular conditions include, but are not limited to, disorders such as deep venous thrombosis, cerebral ischemia, including stroke, and pulmonary embolism. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The methods of the invention are useful for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack is one in which the blood flow to the brain is interrupted only briefly and causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption in blood flow to the brain resulting from either a thromboembolism. A stroke causes a loss of neurons typically resulting in a neurologic deficit that may improve but that does not entirely resolve. Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms.

The rapid absorption of HLGAGs, such as UFH or LMWH, after inhalation as dry particles can be very valuable in the treatment of venous thromboembolism. Intravenous administration of UFH has been used widely for treatment of venous thromboembolism in combination with oral Warfarin. Due to the improved efficacy and reduced risks, however, LMWHs have been increasingly used as an alternative to intravenous UFH in treatment of venous thromboembolism. It has been established that efficacy of heparin therapy depends on achieving critical therapeutic levels (0.35-0.7 U/ml anti-factor Xa activity) within the first 24 hours of treatment. Intrapulmonary delivery of heparin particles to achieve rapid therapeutic levels of heparin in the early stage of thromboembolism, could also be combined with either s.c. administration of LMWHs or formulated heparin particles for prolonged antithrombotic/anticoagulant effect.

The methods of the invention in some embodiments are directed to the treatment of acute thromboembolic stroke using HLGAGs. An acute stroke is a medical syndrome involving neurological injury resulting from an ischemic event, which is an interruption in the blood supply to the brain.

An effective amount of a HLGAG preparation alone or in combination with another therapeutic for the treatment of stroke is that amount sufficient to reduce in vivo brain injury resulting from the stroke. A reduction of brain injury is any prevention of injury to the brain which otherwise would have occurred in a subject experiencing a thromboembolic stroke absent the treatment of the invention. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone.

The pharmaceutical HLGAG preparation may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, warfarin, coumadin, dicumarol, phenprocoumon, acenocoumarol, ethyl biscoumacetate, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol*; v. 25 (7 supp), p. 18S-22S (1995); Holmes, et al, *J Am Coll Cardiol*; v.25 (7 suppl), p. 10S-17S (1995)). Thrombolytic agents include, but are not limited to, plasminogen, $a_2$-antiplasmin, streptokinase, antistreplase, tissue plasminogen activator (tPA), and urokinase. "tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin. The fibrinolytic activity of tPA may be determined by any in vitro clot lysis activity known in the art, such as the purified clot lysis assay described by Carlson, et. al., *Anal. Biochem.* 168, 428-435 (1988) and its modified form described by Bennett, W. F. Et al., 1991, Supra, the entire contents of which are hereby incorporated by reference.

Pulmonary embolism as used herein refers to a disorder associated with the entrapment of a blood clot in the lumen of a pulmonary artery, causing severe respiratory dysfunction. Pulmonary emboli often originate in the veins of the lower extremities where clots form in the deep leg veins and then travel to lungs via the venous circulation. Thus, pulmonary embolism often arises as a complication of deep venous thrombosis in the lower extremity veins. Symptoms of pulmonary embolism include acute onset of shortness of breath, chest pain (worse with breathing), and rapid heart rate and respiratory rate. Some individuals may experience haemoptysis.

The products and methods of the invention are also useful for treating or preventing atherosclerosis. Heparin has been shown to be beneficial in prevention of atherosclerosis in various experimental models. Due to the fast and more direct access to the endothelium of the vascular system, inhaled heparin is useful in prevention of atherosclerosis. Atherosclerosis is one form of arteriosclerosis that is believed to be the cause of most coronary artery disease, aortic aneurysm and atrial disease of the lower extremities, as well as contributing to cerebrovascular disease.

Due to its fast absorption and variable elimination rate, HLGAG particles with or without excipients can be used as an alternative for the intravenous heparin for surgical and dialysis procedures. For example, HLGAG particles can be inhaled prior to surgery by volunteer inhalation or passively inhaled via trachea tube during the anesthesia prior to or during the surgery. Surgical patients, especially those over the age of 40 years have an increased risk of developing deep venous thrombosis. Thus, the use of HLGAG particles for preventing the development of thrombosis associated with surgical procedures is contemplated. In addition to general surgical procedures such as cardiac-pulmonary by-pass surgery, coronary revascularization surgery, orthopedic surgery, prosthesis replacement surgery, and abdominal surgery, the methods are also useful in subjects undergoing a tissue or organ transplantation procedure.

In addition, pulmonary inhalation of dry aerosolized heparin is valuable in treatment of respiratory diseases such as asthma, allergy, emphysema, adult respiratory distress syndrome (ARDS), lung reperfusion injury, ischemia-reperfusion injury of the lung, kidney, heart, and gut, and lung tumor growth and metastasis, since heparin is known to have anti-inflammatory and anti-allergic properties. Heparin is also a well established inhibitor of elastase and tumor growth and metastasis. We have shown that the dry aerosolized heparin particles are capable of inhibiting elastase induced lung injury in an acute lung emphysema model. Asthma is a disorder of the respiratory system characterized by inflammation, narrowing of the airways and increased reactivity of the airways to inhaled agents. Asthma is frequently, although not exclusively, associated with atopic or allergic symptoms. Asthma may also include exercise induced asthma, bronchoconstrictive response to bronchostimulants, delayed-type hypersensitivity, auto immune encephalomyelitis and related disorders. Allergies are generally caused by IgE antibody generation against allergens. Emphysema is a distention of the air spaces distal to the terminal bronchiole with destruction of alveolar septa. Emphysema arises out of elastase induced lung injury. Heparin is capable of inhibiting this elastase induced injury. Adult respiratory distress syndrome is a term which encompasses many acute defuse infiltrative lung lesions of diverse ideologies which are accompanied by severe atrial hypoxemia. One of the most frequent causes of ARDS is sepsis. Other types of inflammatory diseases which are treatable with HLGAGs are refractory ulcerative colitis, non-specific ulcerative colitis and interstitial cystitis.

In one embodiment, the HLGAG preparations are used for inhibiting angiogenesis. An effective amount for inhibiting angiogenesis of the HLGAG preparation is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. Several of the angiogenic mitogens are heparin binding peptides which are related to endothelial cell growth factors. The inhibition of angiogenesis can cause tumor regression in animal models, suggesting a use as a therapeutic anticancer agent. An effective amount for inhibiting angiogenesis is an amount of HLGAG preparation which is sufficient to diminish the number of blood vessels growing into a tumor. This amount can be assessed in an animal model of tumors and angiogenesis, many of which are known in the art. Angiogenic disorders include, but are not limited to, neovascular disorders of the eye, osteoporosis, psoriasis, and arthritis.

The HLGAG preparations are also useful for inhibiting neovascularization associated with eye disease. In another embodiment, the HLGAG preparation is administered to treat psoriasis. Psoriasis is a common dermatologic disease causes by chronic inflammation.

HLGAG containing compositions, may also inhibit cancer cell growth and metastasis. Thus the methods of the invention are useful for treating and/or preventing tumor cell proliferation or metastasis in a subject. The terms "prevent" and "preventing" as used herein refer to inhibiting completely or partially the biological effect, e.g., angiogenesis or proliferation or metastasis of a cancer or tumor cell, as well as inhibiting any increase in the biological effect, e.g., angiogenesis or proliferation or metastasis of a cancer or tumor cell.

The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreatic cancer; prostate cancer; rectal cancer; sarcomas; skin cancer; testicular cancer; thyroid cancer; and renal cancer, as well as other carcinomas and sarcomas.

A subject in need of treatment may be a subject who has a high probability of developing cancer. These subjects include, for instance, subjects having a genetic abnormality, the presence of which has been demonstrated to have a correlative relation to a higher likelihood of developing a cancer and subjects exposed to cancer-causing agents such as tobacco, asbestos, or other chemical toxins, or a subject who has previously been treated for cancer and is in apparent remission.

Effective amounts of the polysaccharides are administered to subjects in need of such treatment. Effective amounts are those amounts which will result in the desired biological effect. The desired biological effect will depend on factors such as the type of polysaccharide being administered and the type of disease being prevented or treated. For instance, when the polysaccharide is an HLGAG, the biological effect may be a reduction in cellular proliferation or metastasis, a reduction in inflammation, an inhibition of elastase, prevention of respiratory disease, or prevention of coagulation without causing other medically unacceptable side effects. Such amounts can be determined with no more than routine experimentation. It is believed that doses ranging from 1 nanogram/kilogram to 100 milligrams/kilogram, depending upon the mode of administration, will be effective. The effective percentage of intact HLGAG may be determined with no more than routine experimentation. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including inhalation, oral, subcutaneous, intravenous, etc.

In some aspects of the invention the effective amount of a composition containing HLGAG is that amount effective to prevent invasion of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., Cell 64:327-336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus the HLGAG compositions can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378-383. Matrigel is a reconstituted basement membrane containing type IV collagen, laminin, heparin sulfate proteoglycans such as perlecan, which bind to and localize bFGF, vitronectin as well as transforming growth factor (TGF), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

One advantage of the inhaled heparin is the convenience of administration, which allow self-administration on an outpatient basis. This will enable a faster initiation of treatment with heparin. Thus a subject may keep a device, such as an inhaler, for self administering the polysaccharide when necessary. This is particularly useful for HLGAGs, which in some cases require rapid administration. The polysaccharides may also be administered by a health care professional, e.g. with the use of a tracheal tube. Such methods are well known in the art.

In addition to HLGAGs, other polysaccharides have a diverse array of therapeutic utilities. Chondroitin Sulfate has been used in a complex with cisplatin to reduce the nephrotoxity of cisplatin during chemotherapy. Zhang J S, Imai T, Otagiri M. Effects of a cisplatin-chondroitin sulfate A complex in reducing the nephrotoxicity of cisplatin. *Arch Toxicol* 2000 August; 74(6):300-7). Hyaluronic acid and derivatives thereof have been shown to be a pharmalogical class of slow acting drugs for the treatment of osteoarthritis. Watterson J R, Esdaile J M, Viscosupplementation: Therapeutic Mechanisms and Clinical Potential in Osteoarthritis of the Knee, *J Am Acad Orthop Surg* 2000 October; 8(5):277-284). Chitin, which is a non-sulfated polysaccharide, can be sulfated chemically to produce a modified polysaccharide, e.g., 6-0 sulfated carboxymethyl chitin which is capable of inhibiting lung metastasis of melanoma. Murata J, Saiki I, Makabe T, Tsuta Y, Tokura S, Azuma I, Inhibition of tumor-induced angiogenesis by sulfated chitin derivatives. *Cancer Res* 1991 Jan. 1; 51(1):22-6. Nishiyama Y, Yoshikawa T, Kurita K, Hojo K, Kamada H, Tsutsumi Y, Mayumi T, Kawasaki K. Regioselective conjugation of chitosan with a laminin-related peptide, Tyr-Ile-Gly-Ser-Arg, and evaluation of its inhibitory effect on experimental cancer metastasis. *Chem Pharm Bull* (Tokyo) 1999 March; 47(3):451-3. Polysaccharide isolated from *phellinus linteus* are also useful for treating and preventing melanoma, especially when administered in combination with adriamycin. Han S B, Lee C W, Jeon Y J, Hong N D, Yoo I D, Yang K H, Kim H M. The inhibitory effect of polysaccharides isolated from *Phellinus linteus* on tumor growth and metastasis. Immunopharmacology, 1999 February; 41(2):157-64.). Calcium spirulan, isolated from a blue-green algae, *spirulina platensis*, is a sulfated polysaccharide that is mainly composed of rhamnose and has been demonstrated to inhibit tumor invasion and metastasis. Hayakawa Y, Hayashi T, Lee J B, Ozawa T, Sakuragawa N. Activation of heparin cofactor II by calcium spirulan. *J Biol Chem* 2000 Apr. 14; 275(15):11379-82). Heparin mimetics such as oligosaccharides and pentasaccharides are useful for preventing coagulation and thrombosis. Other glycomimetics have been used for prevention of coagulation as well as treatment of inflammation, cancer and other immunologic disorders. (Barchi, J. J., Curr. Pharm. Des., 2000, 6(4):485-501) Synthetically derived sulfated polysaccharides, such as laminarin are useful for inhibiting heparinase and thus for inhibiting inflammation, tumor progression, etc. (Marchetti, D. et al., Cancer Res., 2000, 60:4767-70). PI-88 is a mixture of highly sulfated oligosaccharides derived from the sulfation of phosphomannum which is purified from a high molecular weight core produced by fermentation of the yeast *pichia holstii*. The main constituent is a pentamannose, however, small amounts of tetrasaccharide and minor amount of hexasaccharide are also present. PI-88 is currently undergoing clinical trials for its anticoagulant/antithrombotic properties. PI-88 is also a potent inhibitor of heparan sulfate binding and inhibits heparinase enzymatic activity. (Parish, C. R., et al., Cancer Res., 1999, 59:3433-41).

Other polysaccharides which are useful according to the invention are polysaccharide vaccine antigens. These antigens can be delivered alone or in combination with standard vaccine adjuvants for the purpose of stimulating an immune response. The polysaccharide antigen is a polysaccharide which is capable of eliciting an immune response against a microorganism in a host. These include, but are not limited to, capsular polysaccharides, lipopolysaccharides and other subcapsular (surface) polysaccharides. Examples of capsular polysaccharides include those isolated from *Haemophilus influenzae, Neisseria meningitidis, Streptococcus pneumoniae, Streptococcus agalactiae, Salmonella typhi, Escherichia coli*, and *Staphylococcus aureus*. Examples of lipopolysaccharides are those isolated from *Neisseria meningitidis, Escherichia coli, Salmonella typhi*, and *Pseudomonas aeruginosa*. Examples of other subcapsular polysaccharides are the common polysaccharide antigen (c-substance) of Group A, B and C Streptococci and the common polysaccharide antigen (c-substance) of *Streptococcus pneumoniae*. The immunology of polysaccharide vaccines has been reviewed by Jennings et al, "The Polysaccharides" (Editor; G. O. Aspinall), Volume 1, 291-329 (1982). See also "Carbohydrate Chemistry," ed. by John F. Kennedy, Clarendon Press, Oxford, 1988; "The Carbohydrates, Chemistry and Biochemistry," ed. by W. Pigman and D. Horton, Academic Press, Inc., 1970; and "Chitin, Chitosan, and Related Enzymes," ed. by John P. Zikakis, Academic Press, Inc., 1984.

In some aspects of the invention also encompasses kits. The kits of the invention include an inhalation apparatus, polysaccharide dry aerosol particle formulation and a detection system. An inhalation apparatus, as used herein, is any device for administering a dry aerosol. This type of equipment is well known in the art and has been described in detail, such as that description found in Remington: The Science and Practice of Pharmacy, $19^{th}$ Edition, 1995, Mac Publishing Company, Easton, Pa., pages 1676-1692. Many U.S. patents also describe inhalation devices, such as U.S. Pat. No. 6,116, 237.

A detection system is particularly useful for the administration of polysaccharides which are dependent upon a therapeutic level in the blood. Detection systems can be invasive or non-invasive. An example of an invasive detection system is one which involves the removal of a blood sample and can further involve an assay such as an enzymatic assay or a binding assay to detect levels of the polysaccharide in the blood. A non-invasive type of detection system is one which can detect the levels of the polysaccharide in the blood without having to break the skin barrier. These types of non-invasive systems include, for instance, a monitor which can be placed on the surface of the skin, e.g., in the form of a ring or patch, and which can detect the level of circulating polysaccharide. One method for detection may be based on the presence of fluorescence in the polysaccharide which is administered. Thus, if a fluorescently labeled heparin is administered and the detection system is non-invasive, it can be a system which detects fluorescence. This is particularly useful in the situation when the patient is self-administering heparin and needs to know the blood concentration or an estimate thereof in order to avoid side effects or to determine when another dose is required.

The polysaccharides may be administered alone or in combination with other polysaccharides or other therapeutic agents, delivered by conventional therapeutic means. In general, when administered for therapeutic purposes, the other therapeutic agents may be applied in pharmaceutically acceptable solutions. Such preparations may routinely contain pharmaceutically acceptable concentrations of salt, buffering agents, preservatives, compatible carriers, adjuvants, and optionally other therapeutic ingredients.

The therapeutic agents may be administered per se (neat) or in the form of a pharmaceutically acceptable salt or in a pharmaceutically acceptable carrier. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The term "pharmaceutically-acceptable carrier" as used herein, and described more fully below, means one or more compatible solid or liquid filler, diluents or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being commingled with the therapeutic agents, and with each other, in a manner such that there is no interaction which would substantially impair the desired pharmaceutical efficiency.

Compositions suitable for parenteral administration conveniently comprise a sterile aqueous preparation of the therapeutic agent, which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

A variety of administration routes are available for the other therapeutic agents. Preferred routes of administration include, but are not limited to, oral, parenteral, intramuscular, intranasal, intratracheal, inhalation, ocular, vaginal and rectal.

For oral administration, the therapeutic agents can be formulated readily by combining the active compound(s) with pharmaceutically acceptable carriers well-known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally, the oral formulations may also be formulated in saline or buffers for neutralizing internal acid conditions or may be administered without any carriers. For buccal administration, the compositions may take the form of tablets or lozenges formulated in conventional manner.

The therapeutic agents, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

The therapeutic agents may also be formulated in rectal or vaginal compositions such as suppositories or retention enemas, e.g., containing conventional suppository bases such as cocoa butter or other glycerides.

In addition to the formulations described previously, the therapeutic agents may also be formulated as a depot preparation. Such long-acting formulations may be formulated with suitable polymeric or hydrophobic materials (for example, as an emulsion in an acceptable oil) or ion exchange resins, or as sparingly soluble derivatives, for example, as a sparingly soluble salt.

The therapeutic agents also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro) capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above.

The therapeutic agents are suitable for use in a variety of drug delivery systems. For a brief review of methods for drug delivery, see Langer, Science 249:1527-1533, (1990), which is incorporated herein by reference.

Other delivery systems can include time-release, delayed release or sustained release delivery systems. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

When administered to a patient undergoing cancer treatment, the polysaccharides may be administered in cocktails containing other anti-cancer agents. The polysaccharide compositions may also be administered in cocktails containing agents that treat the side-effects of radiation therapy, such as anti-emetics, radiation protectants, etc.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The following description of experiments performed is exemplary and non-limiting to the scope of the claimed invention.

EXAMPLES

Example 1

Preparation and Pulmonary Delivery of Unformulated Polysaccharide Particles

Introduction

To determine whether pulmonary inhalation of both UFH and LMWH generated pharmacokinetics parameters are similar to that of s.c. injection for rats and for rabbits, several parameters were investigated. To examine the effect of multiple blood withdrawals and pulmonary inhalation on the hematology of circulation, blood samples were collected in the beginning and at the end of the experiments. For examination of the potential pathological effects of inhaled powder on the lung histology, the lungs of rats and rabbits were harvested at the end of the experiments. Another parameter investigated was whole-blood recalcification times (WBRT), which were used to indirectly determine the amount of unfractionated heparins present in the blood.

Materials and Methods

Formulation of heparins: 100% heparin (UFH and ardeparin) particles were prepared by using a coffee grinder to a size of 1-500 μm. This powder was then subjected to size separation by sieving through the sieves of mesh sizes 20, 53, 75, and 106 μm. As a result, powder with sizes ranging from 1-500, 1-20, 20-53, 53-75, 75-106 and 1-53 μm were obtained. Dry powders incorporating DPPC were prepared by combining ardeparin (93 IU/mg, anti-Xa) (Celcus, OH) with DPPC (Sigma Chemical Co., MO) using a standard single-step spray-drying process and the particles were analyzed as described (Ben-Jebria, etc., Pharmaceutical Research, 16: 555-561, 1999; Wang, etc., Journal of aerosol medicine, 12: 27-36, 1999). In vitro and in vivo activity assays showed no loss of activity of ardeparin due to the formulation processes.

Animal Models

Rats: For the rat model, male rats weighing 350-450 g (Charles River Laboratories, Wilmington, Mass.) were housed for 5-7 days prior to experiments. Rats were fed on rat chow and tap water ad libitum. After anesthetization with Ketamine (80 mg/kg) and Xylazine (10 mg/kg), right carotid artery was isolated and intubated with a Teflon catheter. A 3-way stopcock was connected to the catheter for blood sample collection. The blood collection followed the procedures described by Bjornsson and Levy (Journal of pharmacology and experimental therapeutics, 210: 237-242, 1979). Pulmonary inhalation was done with an insufflator (Delong Distributors, N.J.) specially designed for powder inhalation in small animals. The device was weighed prior to and after the inhalation to determine the amount of powder inhaled. The inhalation was accomplished by pushing the plunge of the syringe containing 1.5 ml air two to three times. 0.2 ml of blood was withdrawn 0, 15, 30 min., 1, 2, 3, 4, 6, 8, 10, 12, 16, 20 hours after treatment. Blood samples were collected in an aqueous solution of sodium citrate (3.8%; ⅑, v/v), centrifuged 20 min at 2000×g and the resulting plasma was shock frozen and then stored in a −80° C. freezer until assay. Whole-blood samples from UFH-treated rats were tested for whole-blood recalcification times as described below.

Rabbits: For the rabbit model, 2.5-3 kg New Zealand male rabbits were used with 4-5 rabbits per group. Rabbits were allowed to adapt for 7 days and free access to water and food. Ketamine (40 mg/kg) and Xylazine (5 mg/kg) were used to anesthetize the rabbits. A-24 gauze Teflon catheter was inserted into the center auricular artery. The catheter was connected to a heparin cap filled with 0.9% saline solution. Then a 15-cm tracheal tube was inserted into the trachea of the anesthetized rabbits via mouth. Subsequently, the insufflator attached to a straight delivery tube of equal length to that of tracheal tube was inserted through the tracheal tube. The penetration length was controlled to be about 1 or 4 cm above the bifurcation point. LMWH was delivered at doses of 300 and 600 IU/kg, the amount of powder was derived by subtracting the weight of insufflator before and after delivery. 6-7 ml of air in a 10 ml syringe was pushed in with each puff. 0.2 ml of blood was withdrawn 0, 5, 10, 30 min, 1, 2, 3, 4, 6, 8, 10, 12, 14, 18, 24 hours after the inhalation. The first 0.2 ml blood withdrawn was discarded with each withdraw. Blood samples were collected in an aqueous solution of sodium citrate (3.8%; ⅑, v/v), centrifuged at 2000×g for 20 min and the resulting plasma was shock frozen and stored in −80° C. freezer until assay.

Subcutaneous administration and instillation of the heparins: Ardeparin at doses of 300 and 600 IU/kg was also given by subcutaneous injection and by i.v. bolus injection via contralateral marginal ear vein. Blood samples were collected 0, 3, 5, 10, 15, 30 min, 1, 2, 3,4, 6, 8, 12 hours after i.v. injection and processed as described above. Ardeparin was also instilled through the trachea of the rabbits (n=3) at 300 and 600 IU/kg in saline (1 ml/kg) via an intubated trachea tube. The plasma was collected at indicated times and analyzed for anti-Xa assay as described.

Pulmonary ravage study: To determine the rate of disappearance of heparin from the lungs of rabbits after inhalation, lungs were harvested en bloc 0, 5, 30 min, 1, 2, 4, 6, 8 hours after either inhalation or instillation of ardeparin with two rabbits used for each time point. The trachea was cannulated with an 18G animal feeding needle and lavaged with five sequential aliquots of 6 ml normal saline. Lavage fluid was centrifuged at 2000×g for 10 min. The supernatant was shock frozen immediately and transferred to −80° C. until assay. The resulting cell pellets were resuspended in saline, homogenized, and centrifuged. The supernatant was tested for anti-Xa activity. The lavaged lungs were homogenized in saline (1 g in 5 ml saline) with a polytron device. The homogenate was centrifuged at 12,000×g for 10 min. and the supernatant was tested for anti-Xa activity as described below.

Activity assays: Anti-Xa assay was used to monitor plasma LMWH level. Anti-Xa assay was performed by modification of the amidolytic method of Teien and Lie (Thrombosis res. 10: 399-410, 1977) with Coatest heparin test kit by using S-2222 as the chromogenic substrate (Diapharma Group, Inc. Ohio). The detailed procedure was described elsewhere (Liu, etc., PNAS, 94: 1739-1744, 1997). The concentration of ardeparin in unknown samples was calculated by comparing to the calibration curve which was linear in the range of 0.1-0.7 IU/ml. In selected groups, anti-IIa activity was also assayed with S-2238 as substrate according to manufacture's instruction (Diapharma Group, Inc. Ohio). The results were expressed in anti-Xa IU and then in μg/ml.

Calculation of pharmacokinetic parameters. Experimental data, expressed in μg/ml, was utilized for non-linear regression curves based on one-compartmental model (Cornelli and Fareed, Semin thromb Hemost, 25: 57-61, 1999) by using SigmaPlot program with the method of extended least squares. From the kinetic curves, the following parameters were calculated: the area under curve (AUC expressed in $\mu g \cdot h \cdot ml^{-1}$), the time corresponding to the peak of maximum concentration ($t_{max}$ expressed in h); the highest concentration ($C_{max}$, expressed in μg/ml); absorption rate constant (Ka expressed in $h^{-1}$); absorption half-life ($t_{1/2}$ expressed in h); elimination rate constant (Ke express in $h^{-1}$); half-life of apparent elimination ($t_{1/2}e$ expressed in h). The AUC (0-t) was calculated using the trapezoidal rule (Rowland and Tozer, Clinical Pharmacokinetics. Concepts and Applications. 459-461, Lea and Febiger, 1989) and extrapolated to infinity (AUC) by dividing the value of the last measured concentration by the elimination rate constant.

Results

1. Physical properties of heparin particles:

| Geometric diameter (μm) | Mass density g/cm³ | Aerodynamic diameter (μm) | Porosity |
|---|---|---|---|
| 1-500, UFH (100%) | 0.47 ± 0.1 | 1-350 | Nonporous |
| 1-53, UFH (100%) | 0.46 ± 0.1 | 1-35 | Nonporous |
| 20-53, UFH (100%) | 0.44 ± 0.1 | 13-35 | Nonporous |
| 1-3, UFH (60%) DPPC (40%) | 0.3 ± 0.1 | 0.5-1.6 | Nonporous |
| 1-53, ardeparin (100%) | 0.39 ± 0.1 | 1-33 | Nonporous |
| 1-20, ardeparin (100%) | 0.42 ± 0.1 | 1-13 | Nonporous |
| 20-53, ardeparin (100%) | 0.43 ± 0.1 | 13-35 | Nonporous |
| 53-75, ardeparin (100%) | 0.45 ± 0.1 | 35-50 | Nonporous |
| 75-106, ardeparin (100%) | 0.45 ± 0.1 | 50-71 | Nonporous |
| 1-500, ardeparin (100%) | 0.41 ± 0.1 | 1-320 | Nonporous |
| 3-7, ardeparin (40%) DPPC (60%) | 0.15 ± 0.05 | 1.2-2.7 | Nonporous |

2. Heparin particles consisting of 100% UFH were generated with a geometric mean diameter of 1-500 μm by grinding. This powder was then inhaled to the lung of the rats via a tube directly inserted into the trachea. At different time intervals, either the blood was withdrawn or the lungs were lavaged for analysis of heparin level. Once inhaled to the lung, heparin rapidly appeared in the blood circulation causing hypocoagulability of the blood (FIGS. 1*a* and *b*). In the mean time, heparin quickly disappeared from the lung as revealed in the lavage fluid (FIG. 1*b*). More than 70% of the UFH was removed from the lavage fluid in less than 1 hour. The absorption profile of the dry heparin particles was distinct from that of intratrachea instillation of liquid heparin into the rat lungs. The appearance of heparin in the blood after instillation of liquid heparin was very much delayed (tmax>3 hours) and moderate (30-50% increase in whole blood clotting time at 10 times higher doses) compared to that of heparin particle inhalation (tmax<1 hour, 100-200% increase in whole blood clotting time).

3. To study if LMWHs could be similarly delivered, we ground 100% ardeparin with a grinder and sieved the generated particles (1-500 μm) with sieves of different mesh sizes (20, 53, 75, and 106 μm cut off). Ardeparin particles ranges from 1-500, 1-20, 20-53, 53-75, 75-106 and 1-53 μm were obtained. These particles were administered by inhalation to rabbits with an insufflator at 300 and 600 IU/kg via an intubated trachea tube. The same doses were also injected subcutaneously and intravenously for reference. To our surprise, particles of all sizes tested showed significant, fast absorption as indicated by anti-Xa activity assay of the plasma samples (FIGS. 2a-f and Table 1). The characteristics shared by these particles have 1) an extremely short absorption half-life (1-10 min), compared to 1-2 hours after s.c. administration (tmax was reached at about 30 minutes after inhalation); 2) comparable elimination rates to s.c. administration (the elimination half-lives of the tested particles range from about 2-3 hours, which is similar to that of s.c. administration); 3) significant bioavailability (depending on the relative bioavailability to s.c. administration ranges from about 15-50%), and 4) close dose-response relationship (the higher dose is associated with higher peak concentration ($C_{max}$) (30-60% of $C_{max}$ obtained for s.c. administration). It is important to note that these characteristics of dry aerosolized heparin particles are distinct from that pulmonary delivery of liquid heparin (FIG. 2g). Finally, the mean residence time (MRT) value of 100% heparin particles was about the half of that of s.c. administration (Table 1). A close dose-response relationship was also observed for 100% ardeparin particles as shown in FIGS. 2c, d, e and Table 1.

4. To investigate the potential absorption mechanism of dry heparin aerosol, we lavaged the lungs of rabbits after inhalation of 1-53 μm ardeparin particles at indicated time intervals and the heparin level in lavage fluid was determined. In contrast to pulmonary delivery of liquid heparin, the heparin (ardeparin) level in lavage fluid decreased precipitously after inhalation of dry ardeparin particles (FIG. 2f). More than 90% of ardeparin disappeared from the lavage fluid in about 1 hour and base line levels were reached in about 2 hours. Coupled with the rapid appearance of ardeparin in the blood circulation, it is apparent that inhaled dry unformulated heparin was quickly absorbed from the lung.

Figure 3:
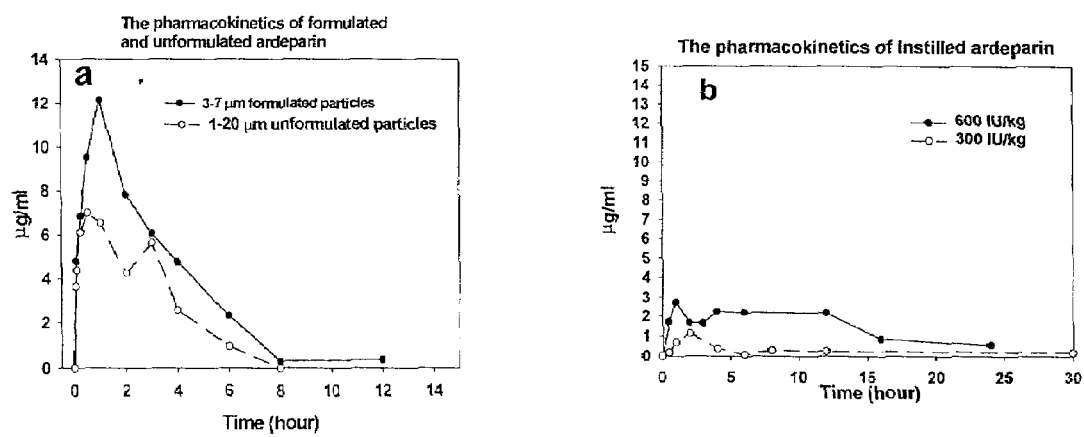
FIG. 3 is a set of graphs depicting a) comparison of pharmacokinetics of formulated ardeparin (40% ardeparin 60% DPPC, 3-7 μm geometric diameter) and unformulated ardeparin (100% ardeparin, 1-20 μm geometric diameter) at 600 IU/kg. b) pharmacokinetics of ardeparin after instillation in rabbits at 300 and 600 IU/kg.
Figure 4:
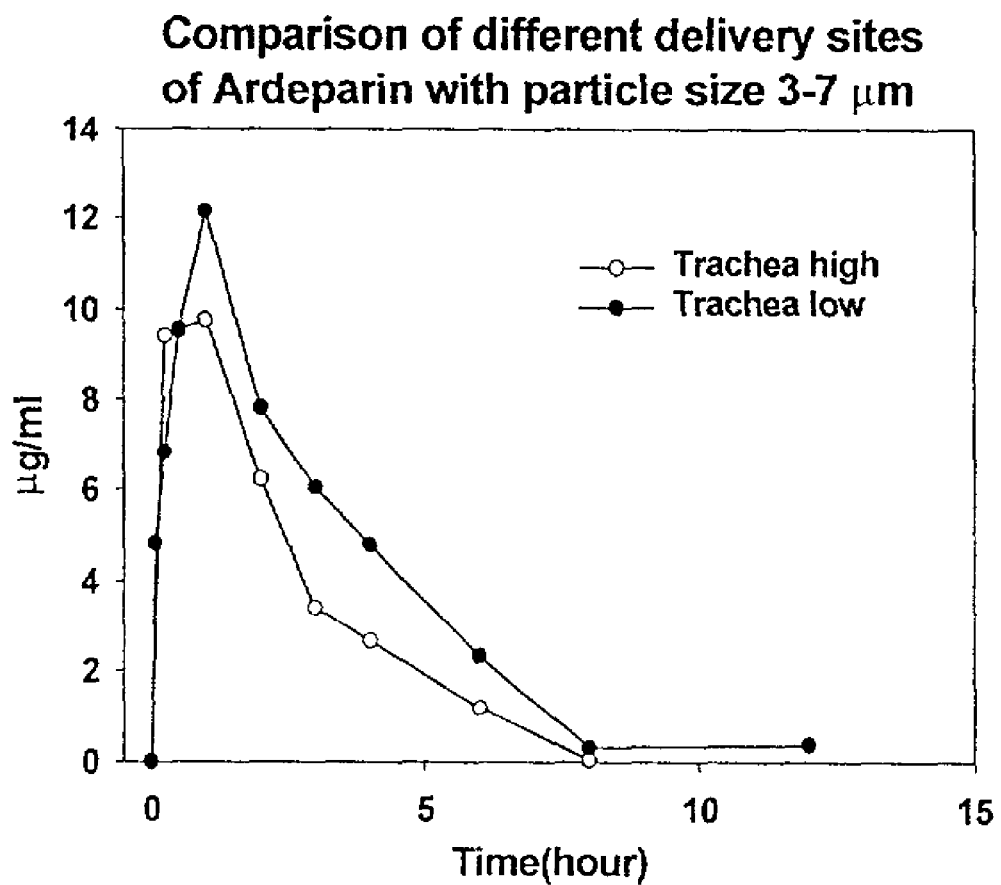
FIG. 4 is a graph depicting the effect of depth of delivery site on the pharmacokinetics of formulated ardeparin particles (3-7 μm, 40% ardeparin 60% DPPC). The delivery tube was placed either 1-2 μm or 4-5 μm above bifurcation point. 6 ml of air was used to aerosolize the powder for the lower tube position and 3 ml of air was used for the higher tube position.
Figure 5:
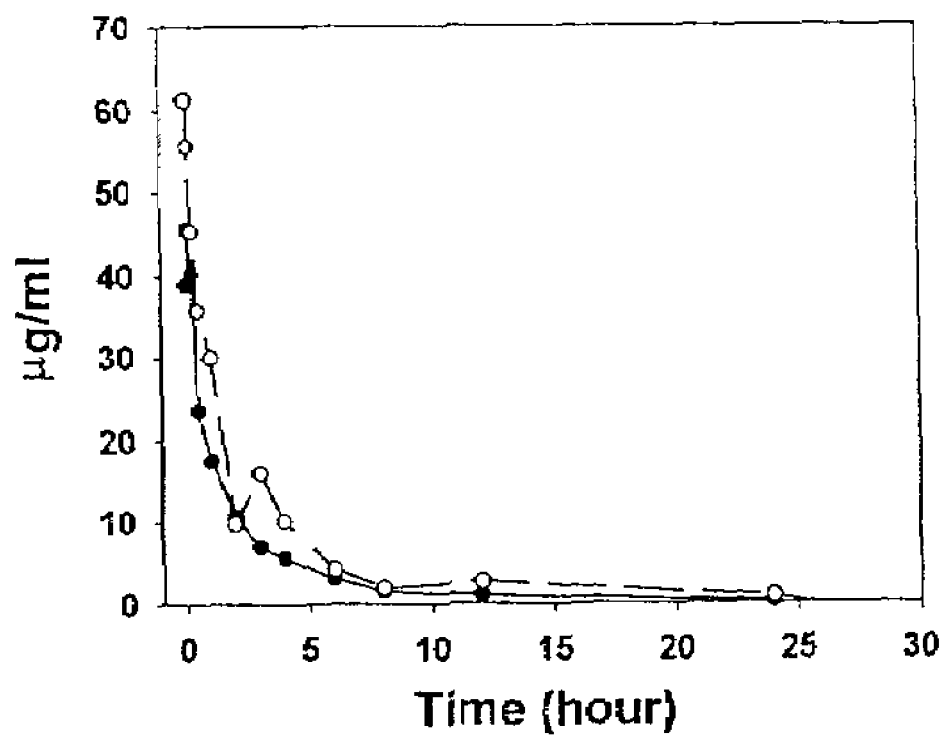
FIG. 5 is a graph depicting the pharmacokinetics of ardeparin after i.v. bolus injection at 300 and 600 IU/kg doses.

Small particles: Since we observed a significant absorption of heparin as 100% heparin particles, it led us to investigate whether modified pharmacokinetics could be achieved by combining heparin with excipients. Naturally occurring lung surfactant DPPC (dipalmitoylphosphatidylcholine) was used as the excipient during the formulation process. Dry ardeparin and UFH particles incorporating DPPC at different percentages were generated by a spray drying procedure. Briefly, heparin dissolved in water was mixed with DPPC in ethanol prior to spray drying with a Buchi 190 spray dryer. The inlet temperature was controlled to be about 110-120° C., and the outlet temperature was controlled to be about 40-50° C. This procedure produced particles sizes of 1-3 μm for UFH and 3-7 μm for ardeparin. The particles were then tested in rabbits at the doses indicated earlier. The pharmacokinetic parameters generated with these small heparin particles (1-3 μm for UFH and 3-7 μm for ardeparin) with DPPC as excipient showed comparable pharmacokinetics to that of 100% UFH and ardeparin particles with a slightly increased absorption and elimination half-lives (FIGS. 1a and 3a; Table 1). However, prolonged biological half-lives, MRT, as well as, bioavailability was also noted for formulated ardeparin. (FIG. 3a, Table 1).

DISCUSSION

It is a generally accepted that a geometric diameter or aerodynamic diameter of 1-5 μm is required for deep lung deposition of the dry aerosol particles. Particles with aerodynamic diameters of 8-10 μm are more likely to deposit in the tracheobronchial region. It is also assumed that the major site of absorption of compounds administered to the respiratory tract is often assumed to be the alveoli since a greater absorption surface and lack of mucociliary clearance is found in the deep lung. Dry aerosol particles have been used to deliver various proteins, peptides and some small molecules. The bioavailability varies substantially depending on the particle properties, method of delivery and experimental protocols. When delivered directly to the lung system via a trachea tube,

TABLE 1

Pharmacokinetic parameters of ardeparin after inhalation as dry aerosol particles of different size distribution and composition in comparison to s.c. administration of ardeparin.

| | 100% Ardeparin 600 IU/kg Inhalation | | | | 100% Ardeparin 300 IU/kg Inhalation | | 40% Ardeprin with DPPC 600 IU/kg inhalation | S.C. | S.C. |
|---|---|---|---|---|---|---|---|---|---|
| | 1-53 μm | 1—20 μm | 20-53 μm | 1-500 μm | 1-53 μm | 1-20 μm | 3-7 μm | 600 IU/kg | 300 IU/kg |
| Ka | 16.59 | 11 16 | 27.3521 | 5 68 | 2.39 | 9.19 | 2.86 | 0.35 | 0.4757 |
| Ke | 0 30 | 0.23 | 0.28 | 0.39 | 0.61 | 0 37 | 0.35 | 0.29 | 0.3681 |
| $t_{1/2a}$ (min) | 2.8 | 3.7 | 1.5 | 7.3 | 7.4 | 4.5 | 14.4 | 120 | 87.4 |
| $t_{1/2e}$ (h) | 2.33 | 2.95 | 2.49 | 1.77 | 1 14 | 1.88 | 1.98 | 2.37 | 1 88 |
| AUC (μg*h/ml) | 19.40 | 28.18 | 27.37 | 33.46 | 8.74 | 12.89 | 43.16 | 70.09 | 41.03 |
| $C_{max}$ | 5.60 | 7 00 | 7.22 | 13.16 | 2.98 | 3.28 | 11.28 | 8.98 | 7 09 |
| $t_{max}$ (h) | 0.25 | 0.35 | 0.17 | 0.51 | 0.76 | 0.60 | 0.84 | 3.14 | 2.38 |
| MRT (h) | 2.50 | 2.76 | 2.83 | 2.52 | 1.86 | 1.64 | 3.04 | 5 29 | 4.41 | some small molecules have shown bioavailability of more than 80% and a fast absorption was also observed. However, up to date, there have been no studies which to the inventors knowledge demonstrate that polysaccharides such as heparin (UFH or LMWHs) can be efficiently delivered as dry aerosol particles. Pulmonary delivery of heparin as liquid aerosol or intratracheal instillation failed to generate efficient absorption and the pharmacokinetics have been unpredictable.

In the present study, we demonstrated the efficient absorption of heparin as dry aerosol particles, with or without excipient. The absorption rate of the inhaled heparin particles is surprisingly fast because heparin molecules are highly negatively charged macromolecules which is not expected to diffuse through the negatively charged/coated air-blood barrier of alveoli. Once absorbed, heparin is eliminated from the body in a manner akin to that of s.c. administration of heparin. A good bioavailability was observed for the unformulated heparin particles, which was further improved by incorporating DPPC as excipient. The incorporation of DPPC into the particles also slowed down the absorption and elimination processes as reflected with prolonged absorption half-life, MRT, and delayed $t_{max}$ (Table 1).

Figure 7:
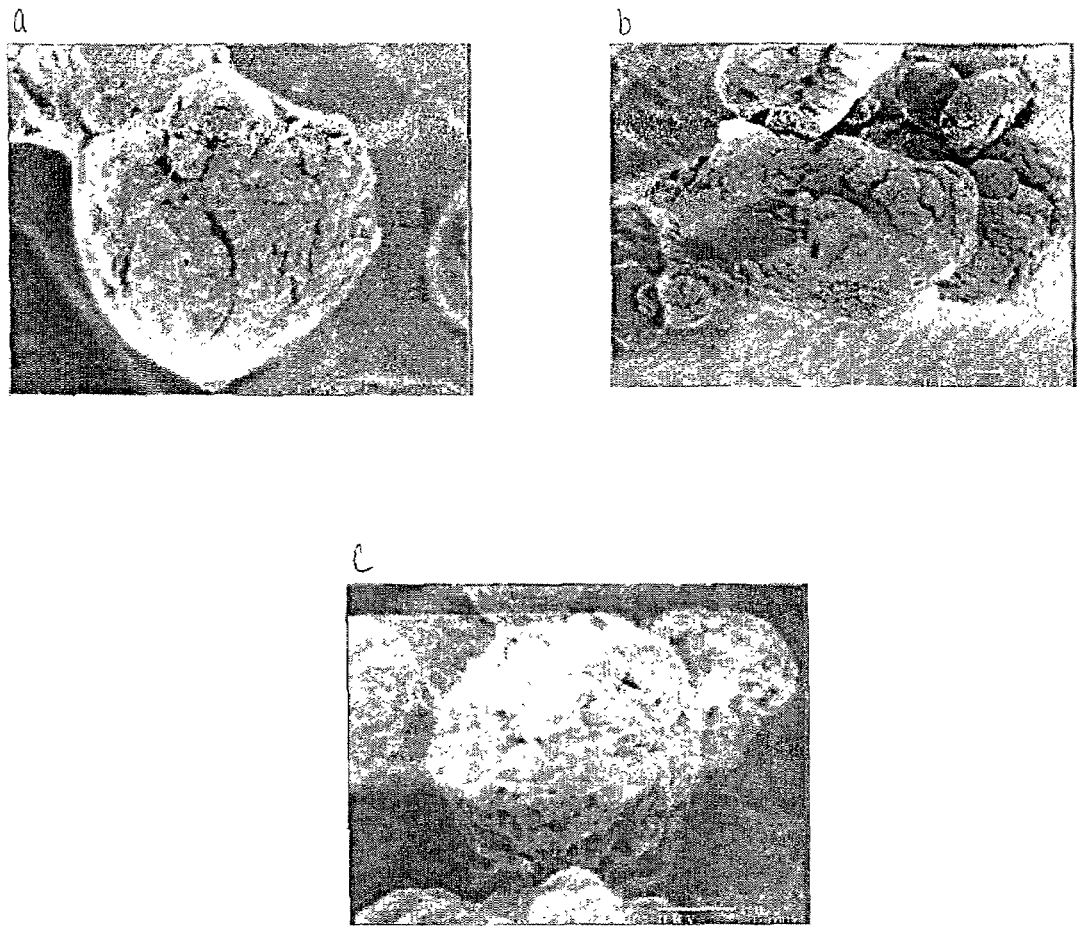
FIG. 7 is a picture depicting the scanning electron microscope (SEM) pictures of heparin particles. The size, porosity, and the texture of the heparin of both formulated and unformulated heparin particles were compared. The images were taken with JEOL JSM-6320 FV Scanning Electron Microscope at 1 KV. a) The SEM of unformulated UFH particles showing a single particle. b) The SEM of unformulated UFH showing multiple particles. c) The SEM of formulated UFH particles (60% UFH 40% DPPC).

What is extraordinary about the unformulated heparin particle pharmacokinetics is that a significant absorption is observed for particles with aerodynamic or geometric diameters larger than 1-5 μm and of any tested mass density. The mass density of the particles tested ranged from 0.15 to 0.47 g/cm$^3$. Particles of different shape showed good absorption (FIG. 7; Table 1). Significant absorption was observed for a wide range of particle size from 1 to 500 μm in geometric diameter. For instance, ardeparin particles of 20-53 μm geometric diameter (aerodynamic diameter 13-35 μm) showed comparable absorption to that of small particles with a geometric diameter of 3-7 μm (aerodynamic diameter of 1.2-2.7 μm). This property of heparin particles is unique and unexpected. The significant absorption of large heparin particles suggest that absorption of heparin after inhalation is likely to occur at multiple levels of respiratory tract and deep lung is likely to be partially responsible for the absorption of heparin. This notion is further supported by the results from the lavage study which showed fast disappearance of inhaled heparin after inhalation of heparin particles.

Another important conclusion drawn from this study is that the pharmacokinetic profiles of heparin can be adjusted by incorporating excipient materials such as DPPC to meet the requirement of a specific clinical application. For example. DPPC was shown here to prolong the biological half-lives of inhaled heparin particles, which generated a more comparable pharmacokinetic profile to that of s.c. administration (FIG. 3a; Table 1). This would allow inhalation of heparin particles as a promising alternative for s.c. administration of LMWHs, which is being widely used in the prevention and treatment of thromboembolic diseases in the clinic.

Example 2

Pulmonary Inhalation of Dry Aerosolized Formulated Polysaccharides Resulted in Efficient Absorption and the Bioavailability of Inhaled Polysaccharides Closely Resemble that of S.C. Injection.

Methods

Heparin Formulations: Preweighed UFH (178 USP/mg) or LMWH (93 IU/mg, anti-Xa) (Celcus, OH) was dissolved in water, and DPPC was dissolved in ethanol. Then, two solutions were mixed at various ratios prior to spray drying. In vitro and in vivo activity assays showed no loss of activity of either UFH or LMWH due to the formulation processes.

Pharmacokinetic Parameters

Hematology: Blood samples were collected in the beginning and at the end of the experiment and submitted for analysis. Blood features measured included white cell, red blood cell, and platelet counts, hematocrit, and hemoglobin and all were measured using standard procedures.

Histology: The lungs of rats and rabbits were harvested at the end of the experiments. The lungs were fixed with formalin, paraffin embedded, sectioned, and stained with hematoxylin and eosin staining using standard procedures. The stained sections were examined with a light microscope for pathological changes.

Activity assays: Whole-blood recalcification times (WBRT) were used to indirectly determine the amount of unfractionated heparins present in the blood as described (Ameer, etc, (1999) *Biotechnol Bioeng* 63, 618-24). 0.2 ml blood samples were collected into tubes containing 3.8% sodium citrate (⅑, v/v). Initially, 0.2 ml of citrated blood was added to Hemochron ACT test tubes containing glass particles (CardioMedical Products, Rockaway, N.J.). Next, 0.2 ml of 0.025 M $CaCl_2$ was added to the test tube and the Hemochron-801 clot-timer machine (CardioMedical products, Rockaway, N.J.) was immediately started. The test tube was gently mixed for 10 sec., and inserted into the test well of the Hemochron 801. The time required for a clot to form was recorded. The unknown samples were compared to a standard curve, which was linear in the range of 0-4 USP units heparin/ml blood.

Calculation of pharmacokinetic parameters: This was performed as described above.

Results

Figure 2:
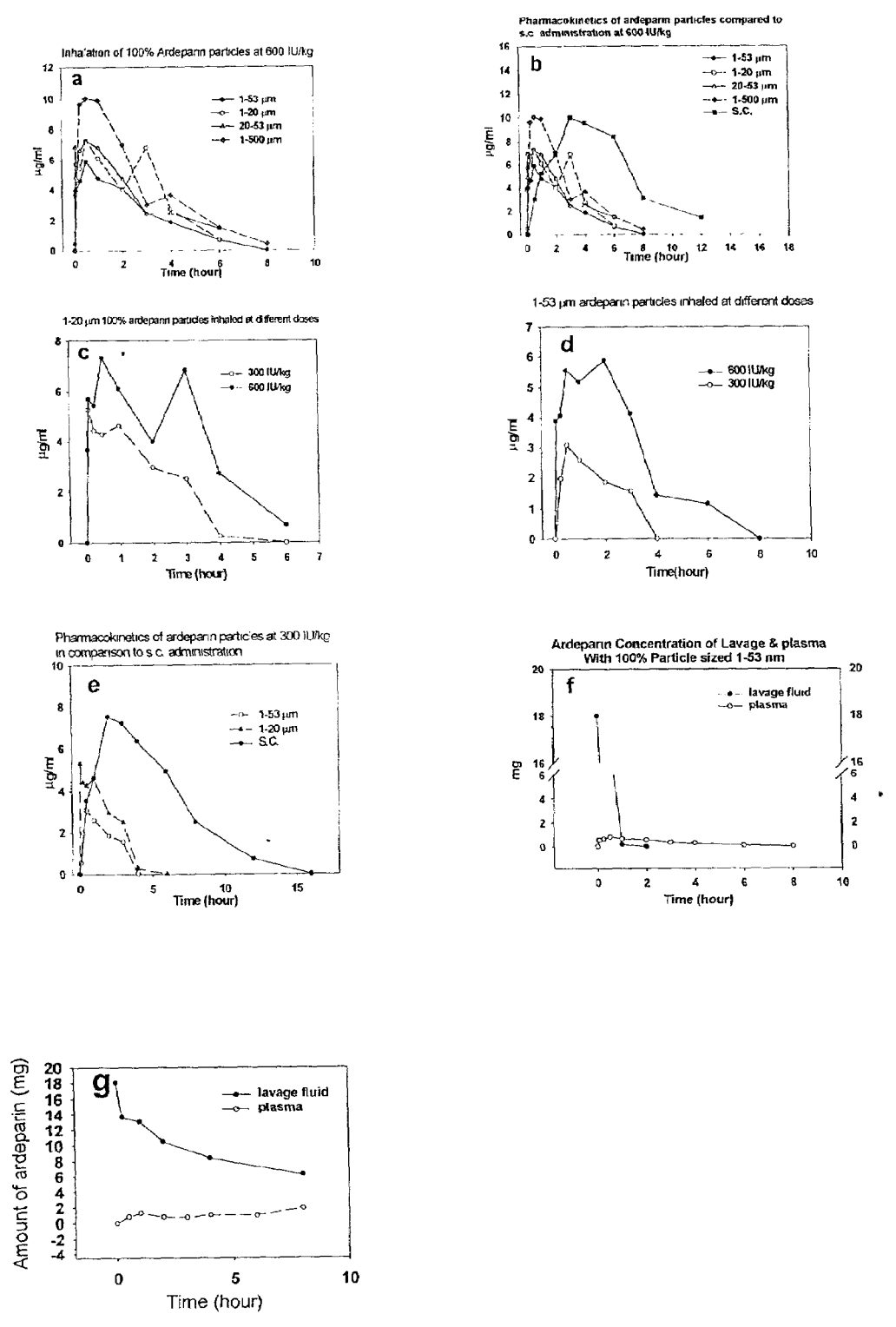

Pulmonary inhalation of dry aerosolized heparins in rats and rabbits resulted in efficient absorption and the bioavailability of inhaled heparin closely resembled that of s.c. injection as described above. There are noticeable distinctions in pharmacokinetics between s.c. injection and pulmonary inhalation. Independent of doses administered, inhaled heparin generally resulted in faster absorption (FIG. 2; table 1). The absorption half-lives of LMWH for inhalation in rabbits were less than 30 min. compared to more than one hour for s.c. injection (table 1). As a result, the rabbit and rat data generated pharmacokinetic characteristics lies somewhere between i.v. and s.c. injection featuring very short absorption phase followed by exponential elimination phase.

Example 3

Dry Aerosol Inhalation of Heparin is Superior to Liquid Aerosol or Instillation of Heparin To compare to the pulmonary inhalation of liquid heparin, liquid heparin was instilled to rabbits. To determine the rate of disappearance of heparin from the lungs of rats and rabbits after inhalation, plasma was collected and anti-Xa assays of the plasma samples was performed. In addition, lungs of rats were also harvested, lavaged, and tested for anti-Xa activity as described below.

Methods

Instillation of LMWH in Rats: LMWH was instilled through the trachea of the rats and rabbits at 600 IU/kg in 0.3 ml (rats) or 1 ml (rabbits) of saline. 4 rats or 2 rabbits per group were used. The plasma was collected at indicated times and analyzed for anti-Xa assay as described below Pulmonary lavage: To determine the rate of disappearance of heparin from the lungs of rat and rabbits after inhalation, lungs were harvested en bloc 0, 5, 30 min, 1, 2, 4, 6, 8 hours after inhalation with one rabbit per time point and lavage was performed as described above. The trachea was cannulated with an 18G animal feeding needle and lavaged with five sequential aliquots of 3 ml (rats) 6 ml (rabbits) normal saline. Lavage fluid was centrifuged at 2000×g for 10 min. The supernatant was shock frozen immediately and transferred to −80° C. until assay.

Anti-Xa Assay. Anti-Xa assay was performed by modification of the amidolytic method of Teien and Lie as described above.

Results

Instilled heparin only generated mild increase in plasma anti-Xa activity (FIG. 2g). At 600 IU/kg, the absorption was relatively slow and lasted a much longer time compared to s.c. or dry aerosol inhalation. At 300 IU/kg, the appearance of anti-Xa activity in plasma is minimal and very brief. It has been well documented that 8 to 10 times higher doses of heparin is required to produce moderate anticoagulant state of the blood when instilled or inhaled as liquid heparin. Therefore, dry aerosol heparin inhalation drastically improved absorption of inhaled heparin.

Example 4

Inhaled Dry Aerosolized Heparin is Quickly Absorbed into the Blood Circulation

To investigate the mechanism of absorption for dry aerosolized heparin, the disappearance of LMWH from the lavage fluid from the rabbit lung was examined.

Results

At 600 IU/kg, the amount of heparin found in the lavage fluid decreased precipitously in the first hour with an elimination half-life of about 6 minutes (FIG. 2f). More than 90% of the inhaled heparin has disappeared from the lavage fluid after 1 hour of inhalation, while the lung tissue and alveolar macrophage examined consistently showed very low level of heparin. Coupled with the rapid appearance of LMWH in plasma (FIG. 2f) and high bioavailability of inhaled heparin (about 20-60%), the heparin particles deposited on the alveolar surface, may dissolve instantaneously resulting in the release of the heparin content and rapid absorption into the blood circulation. This is consistent with the hydrophilic nature of the heparin and high permeability of the respiratory membrane. Because a majority of the inhaled heparin appeared in the blood, phagocytosis by alveolar macrophage may be insignificant. This is again in sharp contrast to the fate of instilled heparin where a significant amount of heparin was phagocytosized and sequestered. More than 50% of instilled heparin remained in the lavage fluid 1½ hour after instillation, which is also observed in the rat instillation model. A significant amount of heparin remained in the lavage fluid even at 8 hour after instillation of the same dose as the inhalation in rabbits (FIG. 2g). In contrast, heparin level decreased sharply in both rabbit and rat studies (FIGS. 1b and 2f). The results suggests the absorption mechanism and deposition profile of the inhaled dry aerosolized heparin is distinct from that of inhaled liquid heparin.

Example 5

Inhaled Heparin Particles are Effective in Preventing Human Leukocyte Elastase Induced Lung Injury Heparin (both UFH and LMWHs) has been known to inhibit human leukocyte elastase and thereby is therapeutic in elastase induced emphysema. Since dry aerosolized heparin particles have the advantage of delivering the heparin directly to the site of elastase induced injury in the deep lung, the effect of inhaled dry heparin was tested in an acute emphysema model.

Methods

Unformulated ardeparin particles at 600 IU/kg or formulated UFH at 12 mg/kg were administered by inhalation to the rats 1 hour prior to instillation of 250 μg of human sputum leukocyte elastase via the trachea. The rats were kept head up at a 30 degree slope for 30 minutes. The incision was sutured and the rats were allowed to recover. 24 hours later the rats were euthanized; the lungs were harvested en bloc and lavaged. The level of hemoglobin in the lavage fluid was determined by a cholorimetric assay kit from Sigma.

Results

Figure 6:
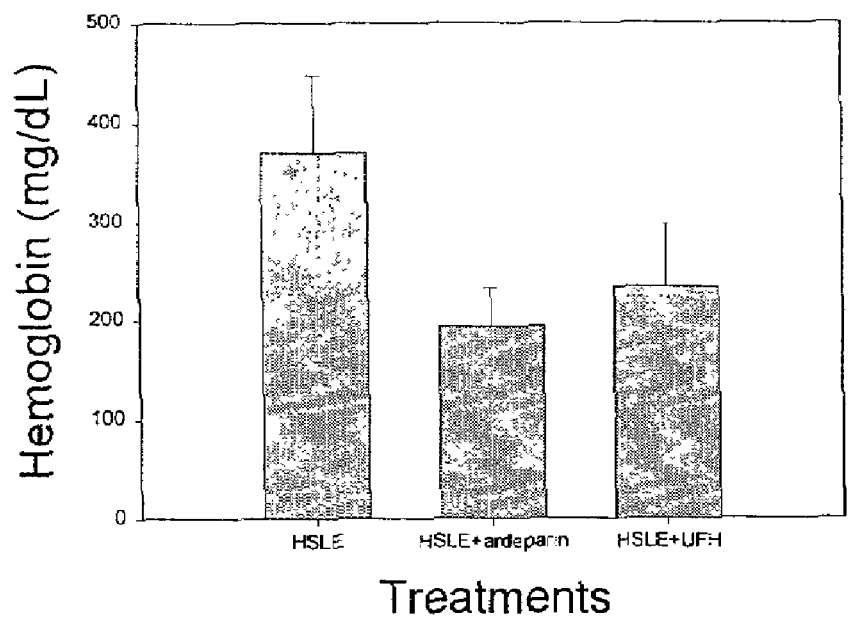
FIG. 6 is a graph depicting the protection of acute injury induced by human sputum leukocyte elastase (HSLE) in lung tissue by pulmonary inhalation of heparin particles. Formulated UFH (60% UFH 40% DPPC, 1-3 μm) at 12 mg/kg or unformulated ardeparin particles (1-20 μm) at 600 IU/kg were administered by inhalation to rats 1 hour prior to instillation of 0.25 ml of HSLE (250 μg). Rats were sacrificed 24 hours later, the lungs were harvested and lavaged. The hemoglobin level in the lavage fluid was assayed. Control group received no heparin was included for comparison.

The inhalation of either heparin particle provided significant protection against the elastase induced acute injury as reflected by hemoglobin level in the lavage fluid (FIG. 6). Ardeparin particles appeared to be more effective, but a direct comparison with UFH was inappropriate due to the dosing difference. Gross examination of the harvested lung also revealed consistent results with less hemorrhage on the lung surface found in the heparin treated group. Furthermore, there was a trend that the distribution of hemorrhage was more limited to the upper lungs in the heparin treated rats, further suggesting heparin particles exerted their protective effect by direct deposition to the site of injury (lower respiratory tract and deep lung).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for delivering a glycosaminoglycan to a subject, comprising, administering to a pulmonary tissue of a subject an unformulated dry glycosaminoglycan having a mean diameter of 1-500 microns.

2. The method of claim 1, wherein the unformulated dry glycosaminoglycan has a mean geometric diameter of 1-200 microns.

3. The method of claim 1, wherein the unformulated dry glycosaminoglycan has a mean geometric diameter of 1-53 microns.

4. The method of claim 1, wherein the unformulated dry glycosaminoglycan has a mean geometric diameter of 1-5 microns.

5. The method of claim 1, wherein the unformulated dry glycosaminoglycan has a mean geometric diameter of 5-53 microns.

6. The method of claim 1, wherein the unformulated dry glycosaminoglycan has a mean geometric diameter of 53-106 microns.

7. The method of claim 1, wherein the glycosaminoglycan is a heparin, a heparan sulfate, or a low molecular weight heparin.

8. The method of claim 1, wherein the unformulated dry glycosaminoglycan has a mean geometric diameter of 10-500 microns.

9. The method of claim 1, wherein the unformulated dry glycosaminoglycan has a mean geometric diameter of 10-250 microns.

10. The method of claim 1, wherein the unformulated dry glycosaminoglycan has a mean geometric diameter of 10-100 microns.

11. The method of claim 1, wherein the unformulated dry glycosaminoglycan has a mean geometric diameter of 100-200 microns.

12. The method of claim 1, wherein the unformulated dry glycosaminoglycan has a mean geometric diameter of 100-150 microns.

13. The method of claim 1, wherein the unformulated dry glycosaminoglycan has a mean geometric diameter of 20-53 microns.

14. The method of claim 1, wherein the unformulated dry glycosaminoglycan has a mean geometric diameter of 53-75 microns.

15. The method of claim 1, wherein the unformulated dry glycosaminoglycan has a mean geometric diameter of 75-106 microns.

16. The method of claim 1, wherein the unformulated dry glycosaminoglycan has a mean geometric diameter of 1-50 microns.

17. The method of claim 1, wherein the unformulated dry glycosaminoglycan has a mean geometric diameter of 1-20 microns.

18. The method of claim 1, wherein the unformulated dry glycosaminoglycan has a mean geometric diameter of 1-100 microns.

19. The method of claim 1, wherein the unformulated dry glycosaminoglycan has a mean geometric diameter of 1-250 microns.

20. The method of claim 1, wherein the unformulated dry glycosaminoglycan has a mean geometric diameter of 5-200 microns.

21. The method of claim 1, wherein the unformulated dry glycosaminoglycan has a mean geometric diameter of 5-30 microns.

22. The method of claim 1, wherein the unformulated dry glycosaminoglycan has a tap density of 0.01-0.4 g/cm3.

23. The method of claim 1, wherein the unformulated dry glycosaminoglycan has a tap density of greater than 0.4 g/cm3.

24. The method of claim 1, wherein the unformulated dry glycosaminoglycan has a tap density of less than 0.4 g/cm3.

* * * * *